United States Patent

Yamazaki et al.

[11] Patent Number: 5,880,835
[45] Date of Patent: *Mar. 9, 1999

[54] APPARATUS FOR INVESTIGATING PARTICLES IN A FLUID, AND A METHOD OF OPERATION THEREOF

[75] Inventors: Isao Yamazaki; Hiroshi Ohki, both of Tsuchiura; Masaetsu Matsumoto; Ryo Miyake, both of Chiyoda-machi; Ryohei Yabe, Katsuta; Hideyuki Horiuchi, Abiko; Shinichi Sakuraba, Katsuta, all of Japan

[73] Assignee: Hitachi, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 703,076

[22] Filed: Aug. 26, 1996

Related U.S. Application Data

[63] Continuation of Ser. No. 308,541, Sep. 24, 1994, abandoned, which is a continuation of Ser. No. 18,371, Feb. 16, 1993, abandoned.

[30] Foreign Application Priority Data

Feb. 18, 1992 [JP] Japan ................................. 4-030383
Nov. 11, 1992 [JP] Japan ................................. 4-300802

[51] Int. Cl.⁶ .................................................. G01N 33/48
[52] U.S. Cl. ............................. 356/336; 356/73; 356/39
[58] Field of Search ................................. 386/335, 336, 386/72, 73, 39; 436/63

[56] References Cited

U.S. PATENT DOCUMENTS

| 5,068,906 | 11/1991 | Kosaka | 382/48 |
| 5,083,014 | 1/1992 | Kosaka | 250/573 |
| 5,099,521 | 3/1992 | Kosaka | 382/6 |
| 5,159,642 | 10/1992 | Kosaka | 356/23 |
| 5,163,095 | 11/1992 | Kosaka | 382/6 |
| 5,272,354 | 12/1993 | Kosaka | 250/574 |
| 5,444,527 | 8/1995 | Kosaka | 356/73 |
| 5,469,375 | 11/1995 | Kosaka | 364/555 |
| 5,521,699 | 5/1996 | Kosaka et al. | 356/73 |

*Primary Examiner*—David B. Hardy
*Attorney, Agent, or Firm*—Antonelli, Terry, Stout & Kraus, LLP

[57] ABSTRACT

In order to investigate particles in a fluid, a flow cell causes the fluid to flow past a sensor which receives light from a continuous light emission system. When the sensor detects a change in light, a particle detector is triggered, which in turn triggers a pulse generator and hence an intermittent light emission system. Light then illuminates the flow cell to allow a CCD camera to photograph the particle. The photographs taken by the CCD camera are analyzed by an image processor. In order to obtain an accurate particle concentration measurement, it is necessary to modify the initial concentration measurement derived from the analysis of particle images by the image processor by a compensation coefficient. This operation is carried out by a concentration compensator. The result may then be displayed. Additional analysis may be carried out by changing the magnification of the CCD camera, or by selecting for analysis only those particles of a selected size or type.

10 Claims, 20 Drawing Sheets

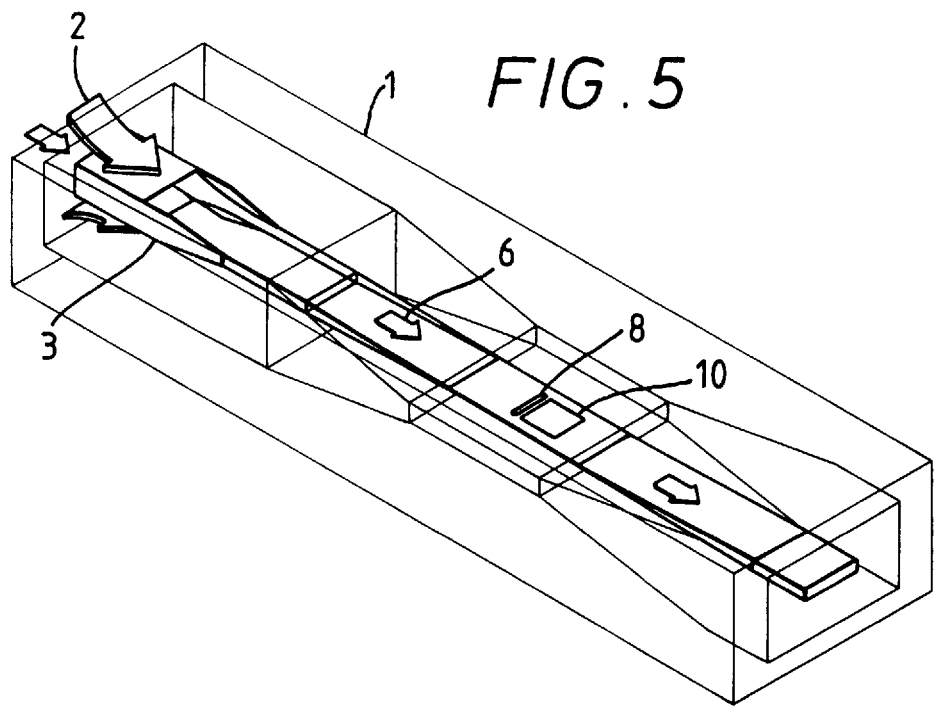
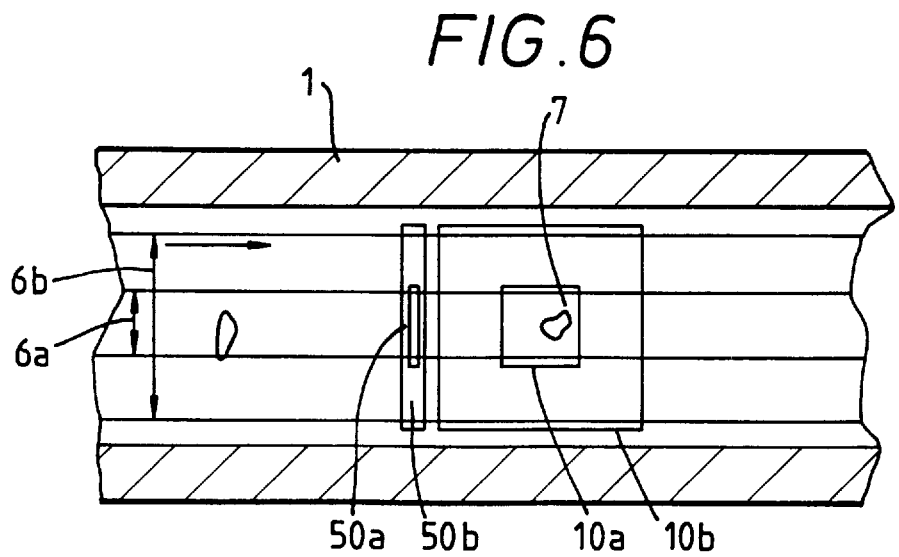

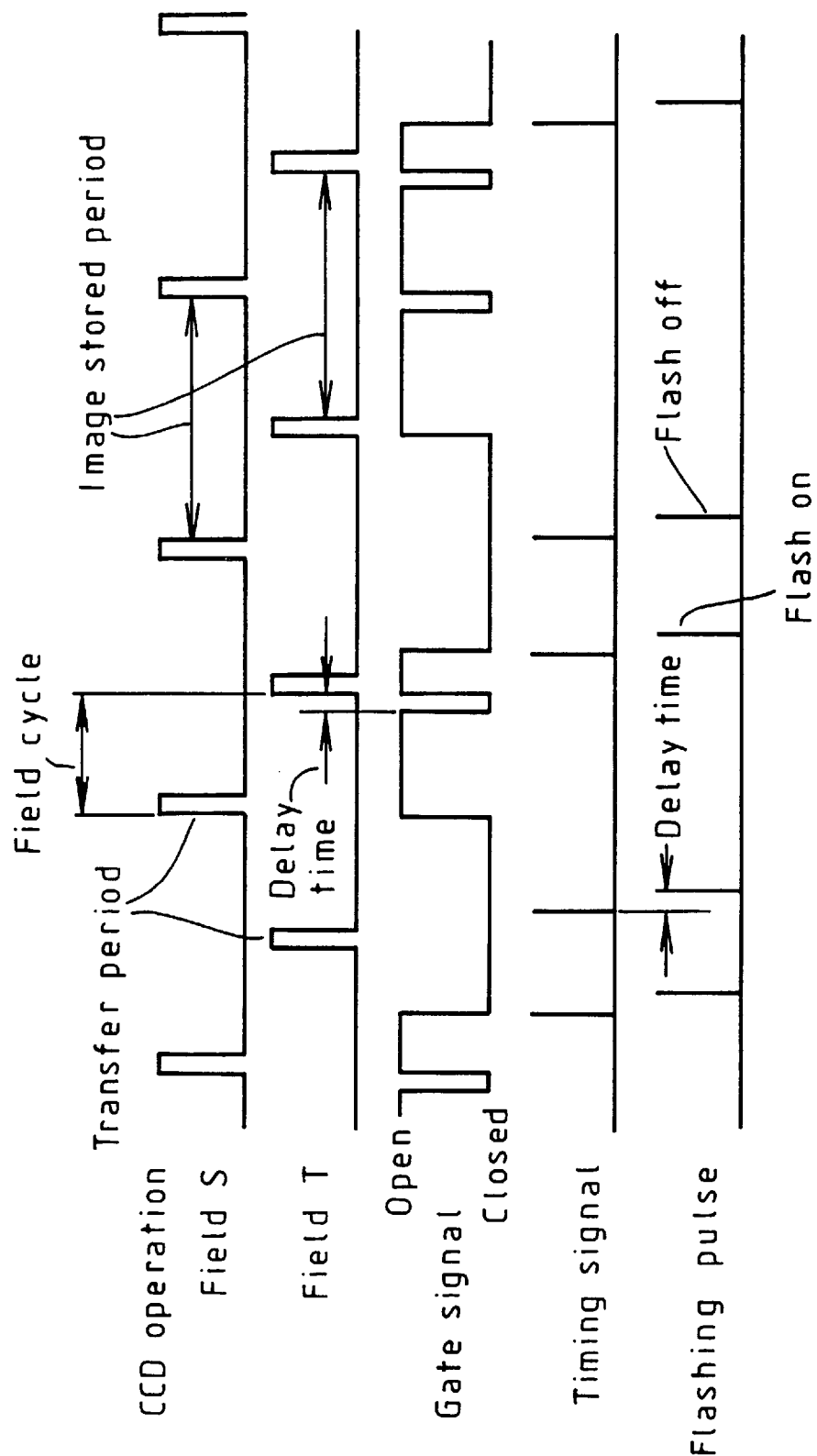

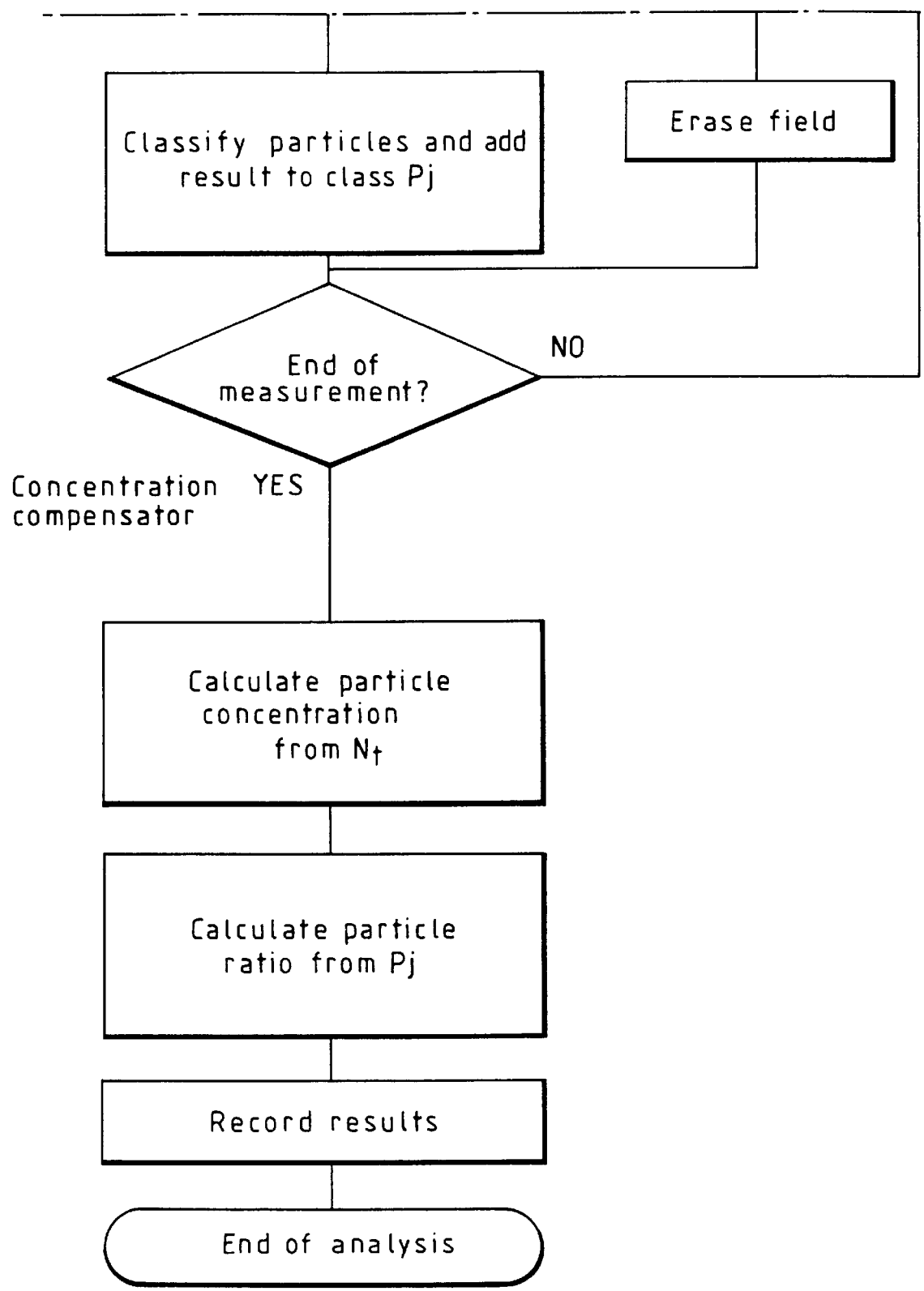
FIG. 9 (CONTD.)

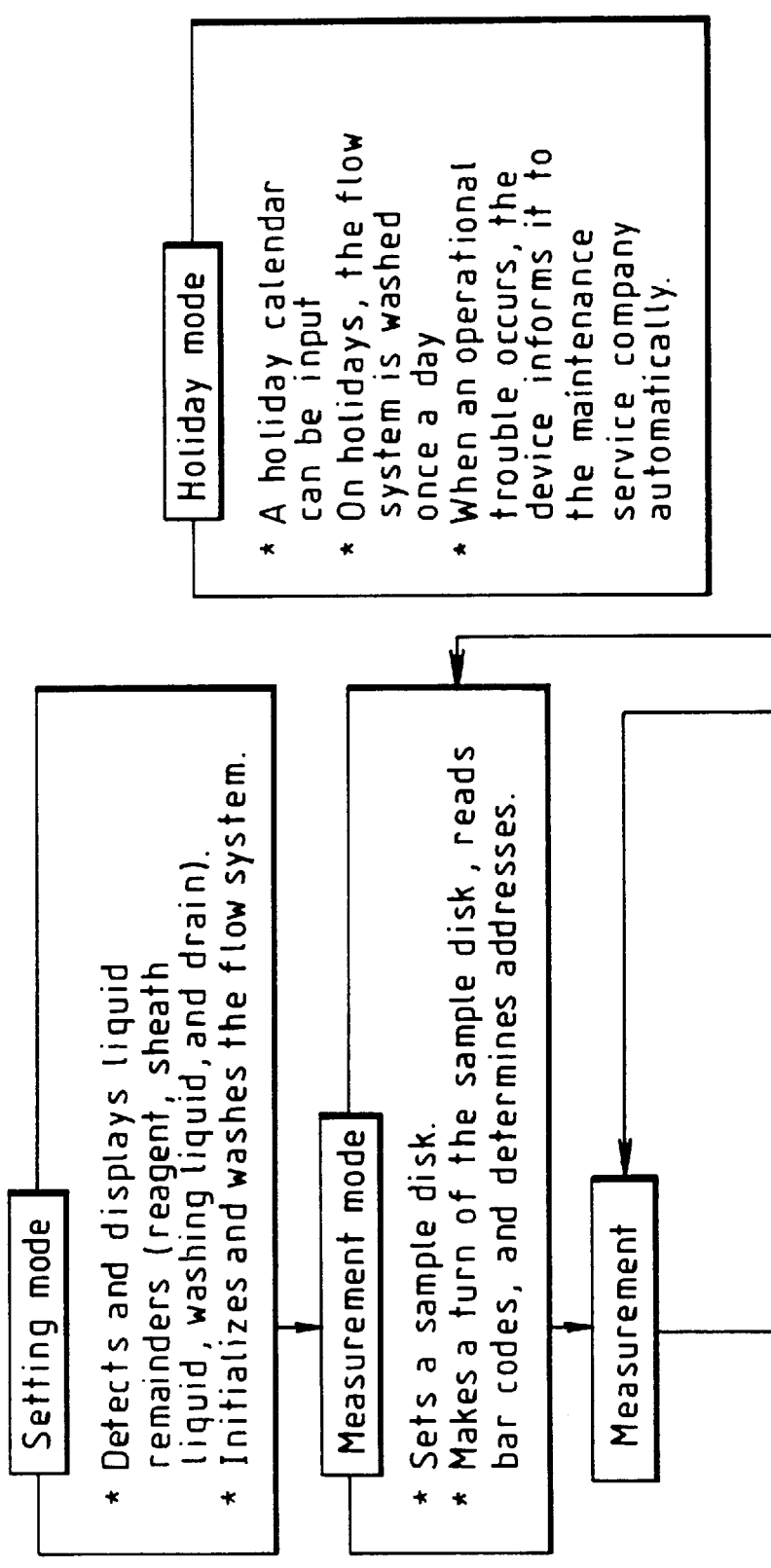

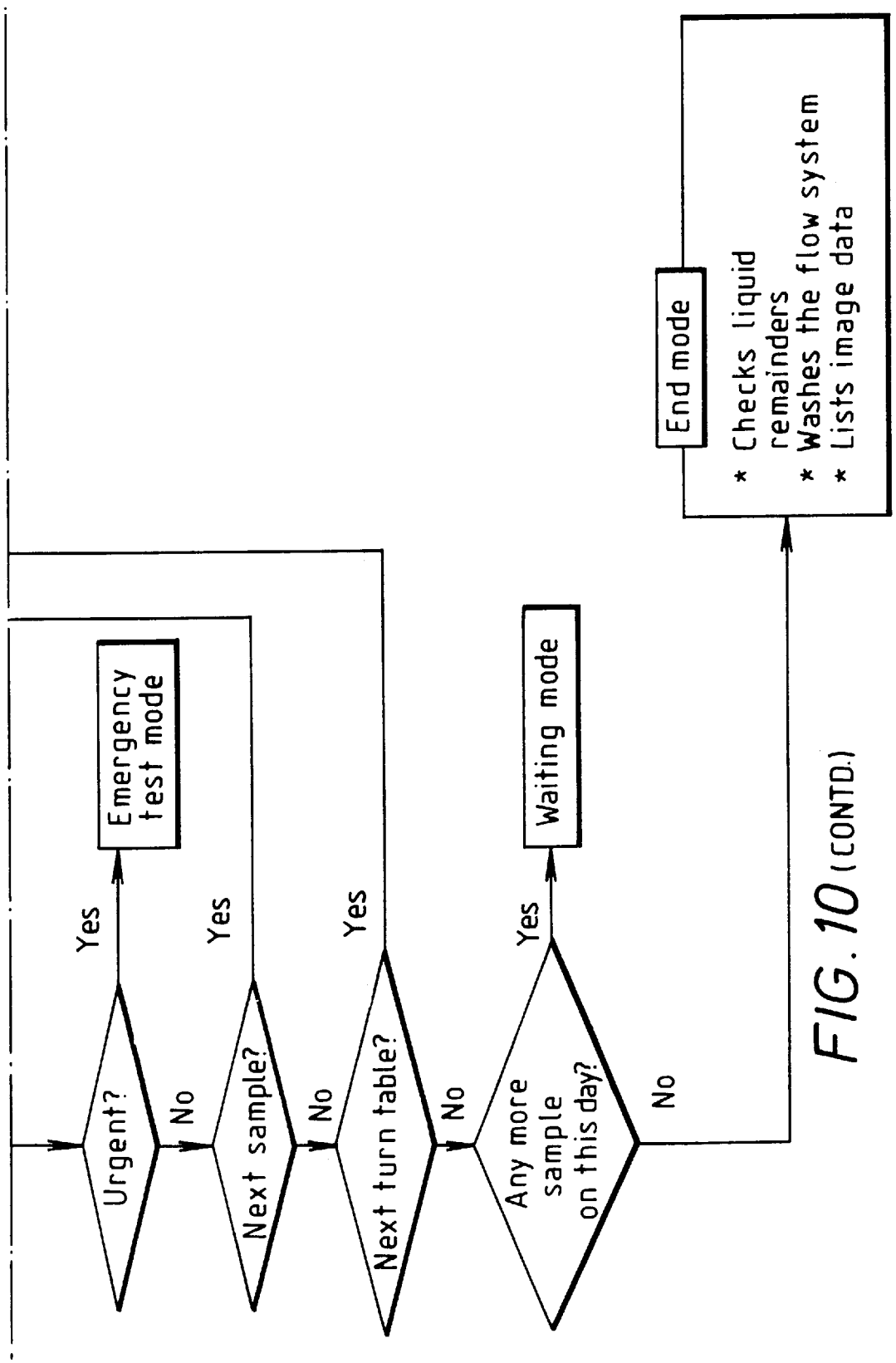
FIG. 10 (CONTD.)

Low magnification mode    High magnification mode
FIG.11(a)
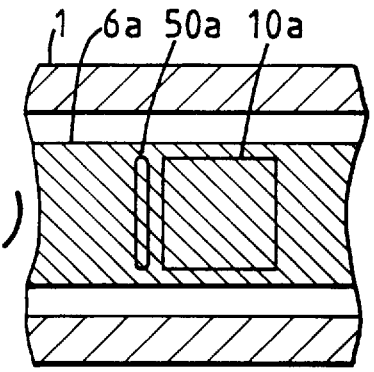 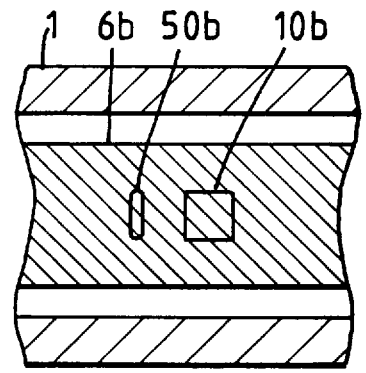
FIG.11(b)
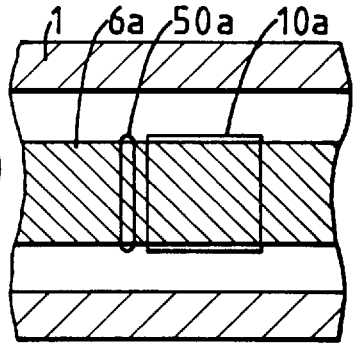 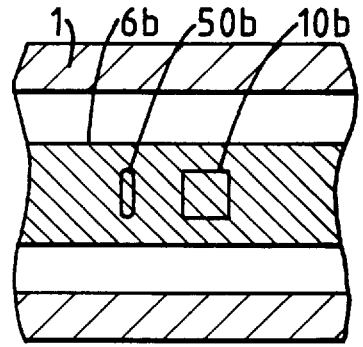
FIG.11(c)
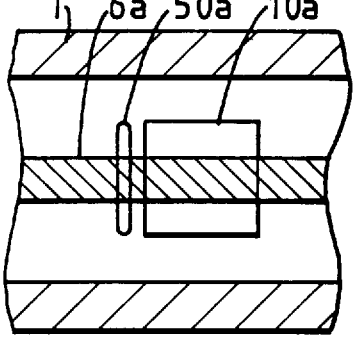 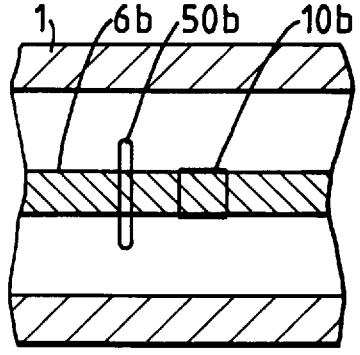
FIG.11(d)
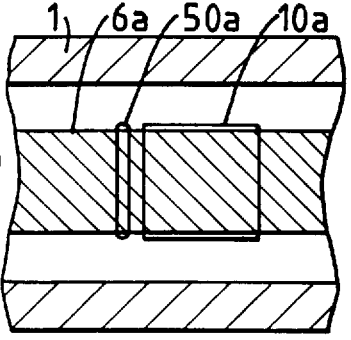 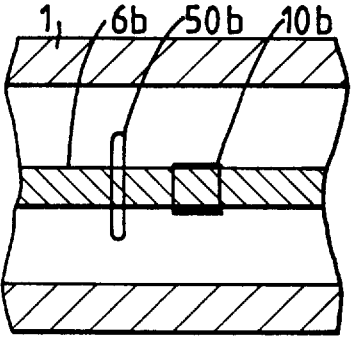

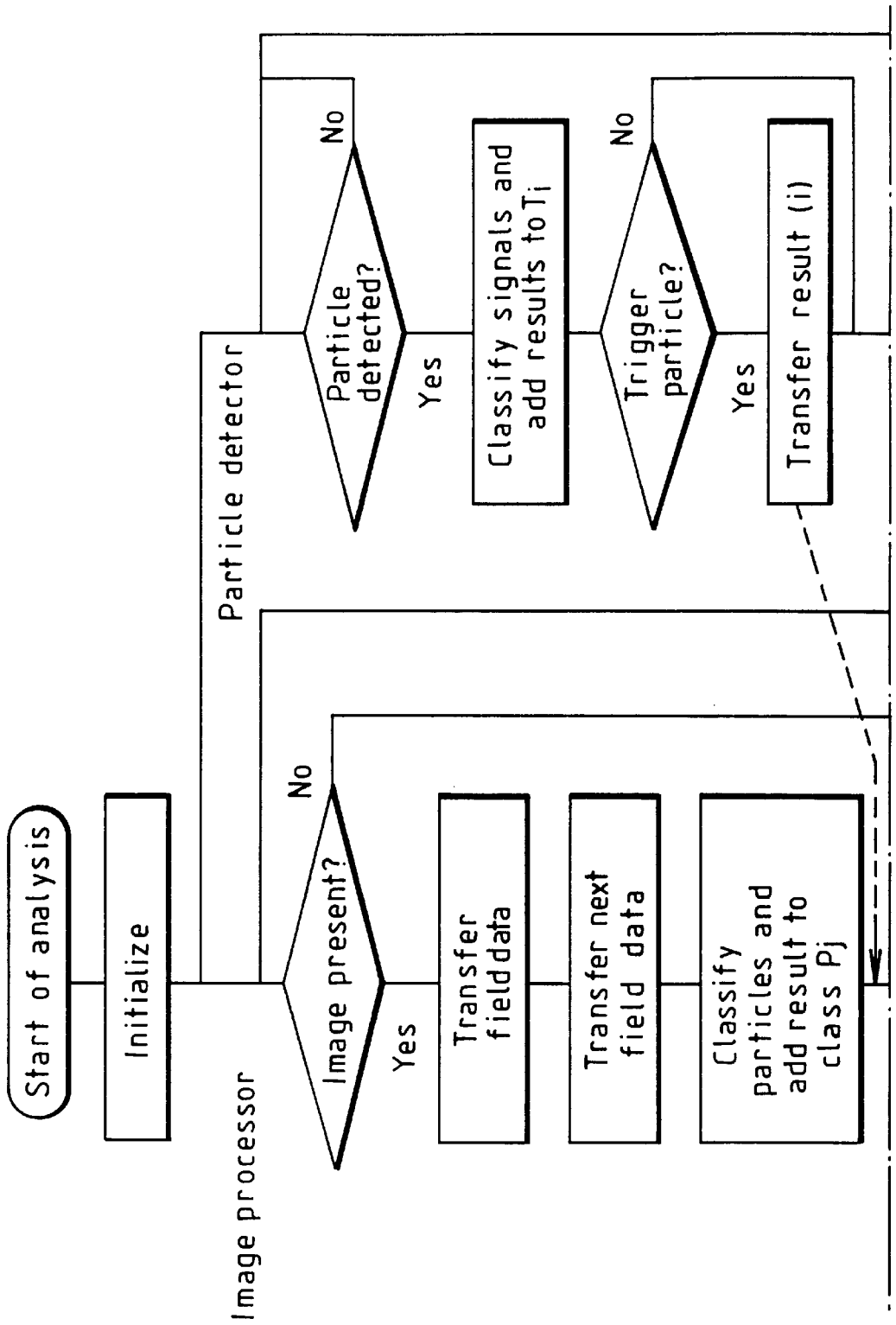
FIG. 13 Concentration analysis flow in embodiment 2

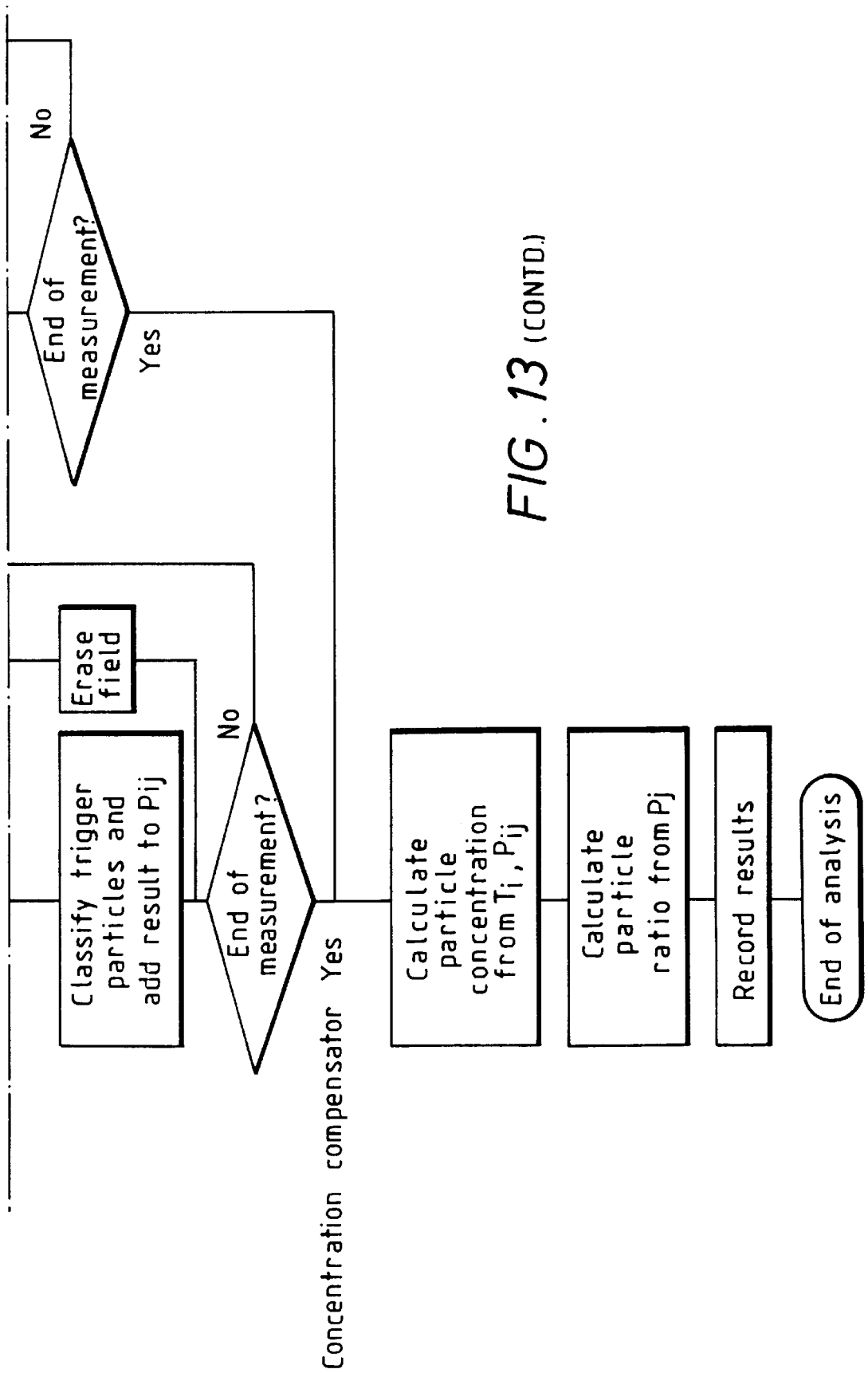
FIG. 13 (CONTD.)

A: Period to photograph a large particle of high concentration
B: Period to photograph a large particle of low concentration
C: Period to photograph a small particle of high concentration
D: Period to photograph a small particle of low concentration E: Period to photograph a particle of high concentration
F: Period to photograph a particle of low concentration

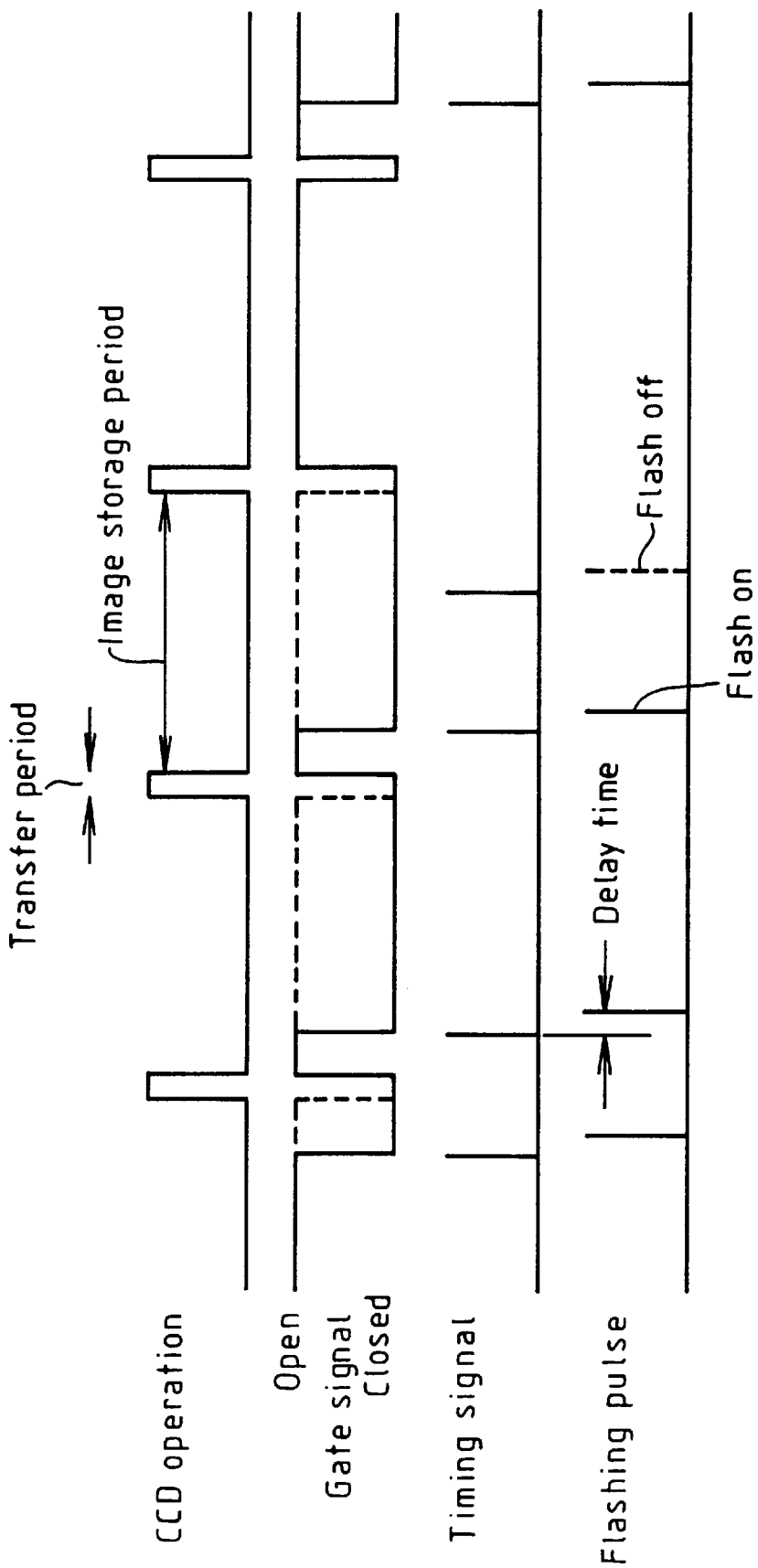

APPARATUS FOR INVESTIGATING PARTICLES IN A FLUID, AND A METHOD OF OPERATION THEREOF

This application is a Continuation of application Ser. No. 08/308,541, filed Sep. 24, 1994, now abandoned which is a continuation of application Ser. No. 08/018,371, filed Feb. 16, 1993, now abandoned.

BACKGROUND OF THE INVENTION

1. Field of the Invention

The present invention relates to an apparatus for investigating particles in a fluid. It is particularly, but not exclusively, concerned with an apparatus for investigating urinary sediments in urine, or blood cells in blood. The present invention also relates to a method of operation of such an apparatus.

2. Summary of the Prior Art

The standard way of analyzing urinary sediments is by shape and size. Samples of urine are separated into liquid and sediment, using a centrifugal separation arrangement. Then, the sediment is dyed and the dyed sediment is studied by means of a microscope. It is important to know the concentration of sediment in the urine, and therefore the rate of centrifugal separation, and the quantities of samples investigated are constant. Originally, such investigation was carried out entirely manually, but attempts have been made to automate the analysis.

In U.S. Pat. No. 4,338,024 (corresponding to JP-A-57-500995), it was proposed that a flow of the fluid containing the particles was guided through a suitable guide means, such as a flow cell, and images were then generated of the flow at a particular point in that flow path. A CCD camera was used as an image means to observe the particles, and an enlarged image could then be generated. The CCD camera was operated periodically, with a fixed time between operations. Furthermore, U.S. Pat. No. 4,338,024 mentioned the use of the images to derive a particle concentration (density) measurement.

Furthermore, in JP-A-63-94156, there was separate detection and imaging of the particles. The particles were detected at a first point in the flow path by a particle detector, and the image means was triggered only when a particle was detected. The image means was located downstream of the particle detector, so that a suitable delay imposed on the triggering could enable a particle detected by the particle detector to be observed by the image means.

SUMMARY OF THE PRESENT INVENTION

The proposal for concentration determination in U.S. Pat. No. 4,338,024 is generally satisfactory when the concentration of particles is high. However, if it is applied to the investigation of particles of a low concentration, a very large number of images must be generated before a suitable concentration measurement can be obtained. In U.S. Pat. No. 4,338,024, the image means (camera) was triggered independent of the number of particles. Therefore, if the concentration of particles was low, images would be generated with no particles present. This poses a particular problem in the analyze of urinary sediments, because such sediments may have a low concentration.

The arrangement proposed in JP-A-63-94156 is more suitable for analyzing particles of low concentration, because the imaging means is only triggered when the particle detector detects that a particle is present in the flow. However, investigations made by the applicants have shown that the images generated by the arrangement of JP-A-63-94156 do not provide a satisfactory concentration measurement. Since the image means is downstream of the detecting means, there is necessarily a delay time between the detection of a particle and the activation of the image means. Any particles passing the image means within this delay time will not be detected. Therefore, the applicants have found that there is an error in the measurement of concentration which increases with increasing concentration.

Therefore, in a first aspect, the present invention proposes that a particle detector is used to detect the particles at a first point in the flow, and the particle detector then triggers an image means. Then, an initial concentration value of the particles in the flow is obtained by direct measurement, but subsequently a modification is made to that initial concentration value using a compensation coefficient, there by to derive an accurate particle concentration measurement.

It is possible, within the present invention, for the modification of the initial concentration value to be made on the basis of a stored compensation coefficient, but it is preferable that use be made of the detection of particles by the particle detector. As has previously been mentioned, the applicants have found that the discrepancy between the concentration as derived from the images and the true concentration is a function of particle concentration. Therefore, if the particle detector detects a relatively large number of particles, the modification to the initial concentration value is greater than when it detects only a few particles.

As has previously been mentioned, the present invention relates to both apparatus and method aspects. Preferably, the particle detector generates a continuous beam of light, so that the particles can be detected by a suitable light detector. In a similar way, the image means may generate an intermittent series of light pulses, which pulses are determined by the particle detector, and the interaction of those light pulses with the particles being picked up by an imaging device.

Once the particles have been detected, and their true concentration determined, it is then possible to classify them on the basis of their concentration.

When a manual investigation of particles in a fluid, such as urinary sediments in urine, is carried out using a microscope, it is possible to vary the magnification of the microscope to investigate particles of different sizes. Neither U.S. Pat. No. 4,338,024 nor JP-A-63-94156 considered the question of magnification changes.

The present invention therefore proposes that the image means which is triggered by a detector upstream of the image means, be arranged to vary each magnification. However, if this is done, it is also necessary to change either or both of the detection dimension of the particle detector, or a dimension of the fluid flow at the image means, in order to obtain an accurate measurement. If, for example, the dimensions of the flow at the image means is significantly wider than the area considered by the image means, then an inaccurate measurement may occur.

This idea of varying the dimension of the detection, or the flow at the image means, in dependence on the magnification may be used with the first aspect of the present invention, but is a second independent aspect. Furthermore, the principle of varying the dimensions of the fluid flow at the image means in dependence on the magnification is applicable to arrangements in which the image means is not controlled by a particle detector upstream of the image means, such as e.g. the arrangement proposed in U.S. Pat. No. 4,338,024.

Furthermore, in a third aspect of the present invention, it is proposed that the image means is arranged to select the magnification on the basis of information from the particle detector, which detects particles in the flow. Again, although this aspect of the present invention may be used in conjunction with either or both of the first and second aspects, it is an independent aspect of the present invention.

A fourth aspect of the present invention is concerned with the investigation operations that are carried out on the particles. In some cases, such as the investigation of urinary sediments in urine, particles of a given size range may be of two or more types, one of which is significantly more common than another or others. A satisfactory measurement of the or each common type of particles may be made in a relatively short time, but a longer period will be needed accurately to analyze the more rare type of particles. Therefore, the fourth aspect of the present invention proposes that all particles of a given size be measured for a first time range, and particles of that size, but of a specified type, investigated within a second time range. The time ranges may overlap, and indeed the time for measurement of the more common particles may be included within the time for measurement of the less common particles.

Furthermore, this fourth aspect of the present invention is not limited to arrangements considering only the size of the particles, and another property of the particles may be chosen instead. Also, it is possible to consider particles of two different types in the two different times.

Again, this fourth aspect of the present invention can be used in conjunction with any of the previous aspects, but is an independent aspect of the present invention.

BRIEF DESCRIPTION OF THE DRAWINGS

Embodiments of the present invention will now be described in detail, by way of example, with reference to the accompanying drawings, in which

FIG. 5 is a perspective view of the structure of a flow cell which may be used in the embodiment of FIG. 1;

FIG. 6 is a sectional top view of the flow cell of FIG. 6;

FIG. 7 shows timing cycles in the embodiment of FIG. 1;

FIG. 10 is a flow-chart illustrating the operating procedure of the embodiment of FIG. 1;

FIGS. 11a to 11d illustrate examples of flow switching in a flow cell of a second embodiment of the present invention;

FIG. 13 is a flow-chart illustrating the Operational Flow of Concentration Analysis in the embodiment of FIG. 12;

FIG. 18 is a timing chart showing the operational timing in the embodiment of FIG. 16;

DETAILED DESCRIPTION

A first embodiment of the apparatus for determining the density of particles in a sample will now be described with reference to FIGS. 1 to 10.

Figure 1:
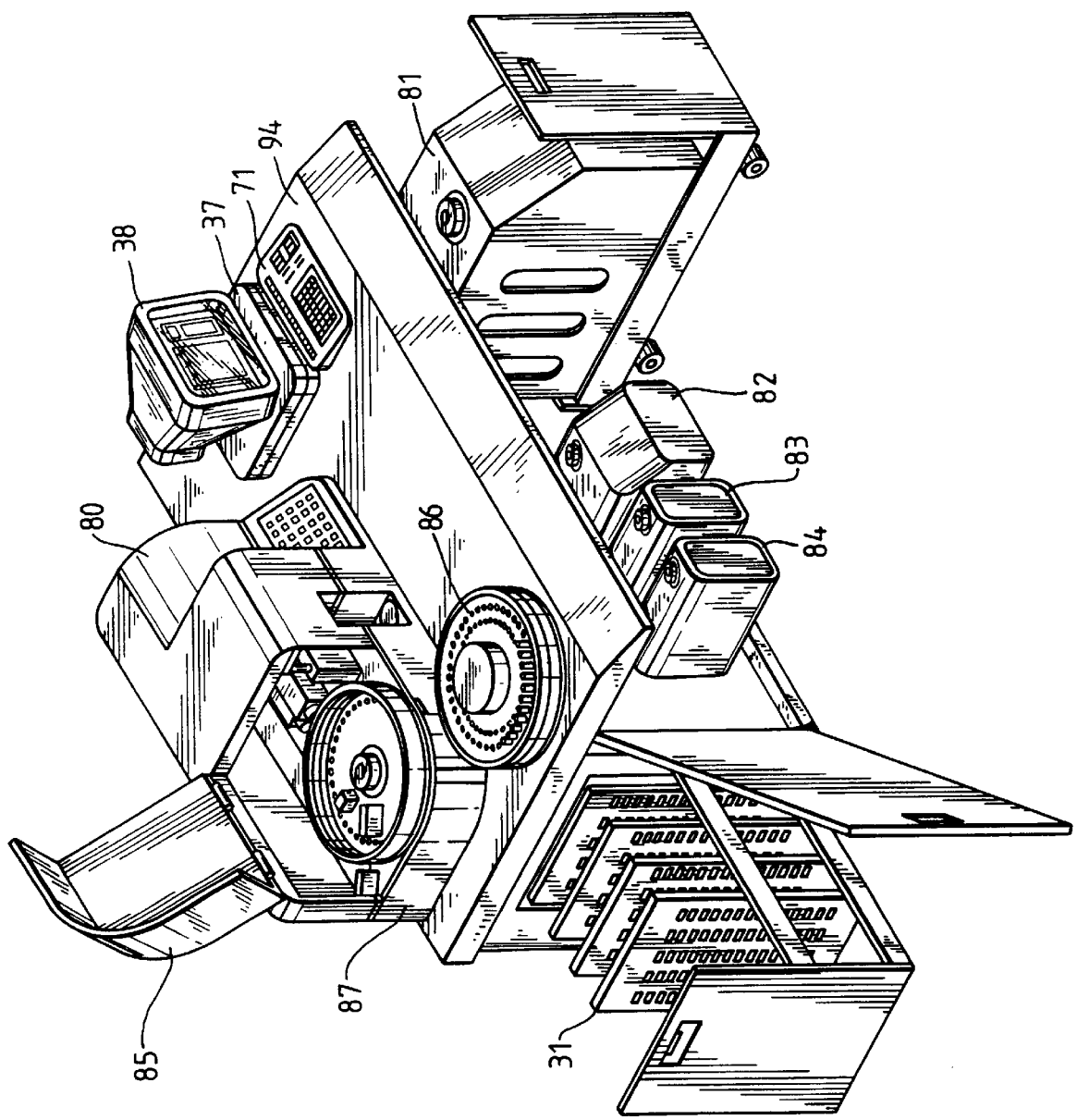
FIG. 1 is a perspective view of the structure of an apparatus for determining the density of particles in a fluid, being a first embodiment of the present invention.
Figure 2:
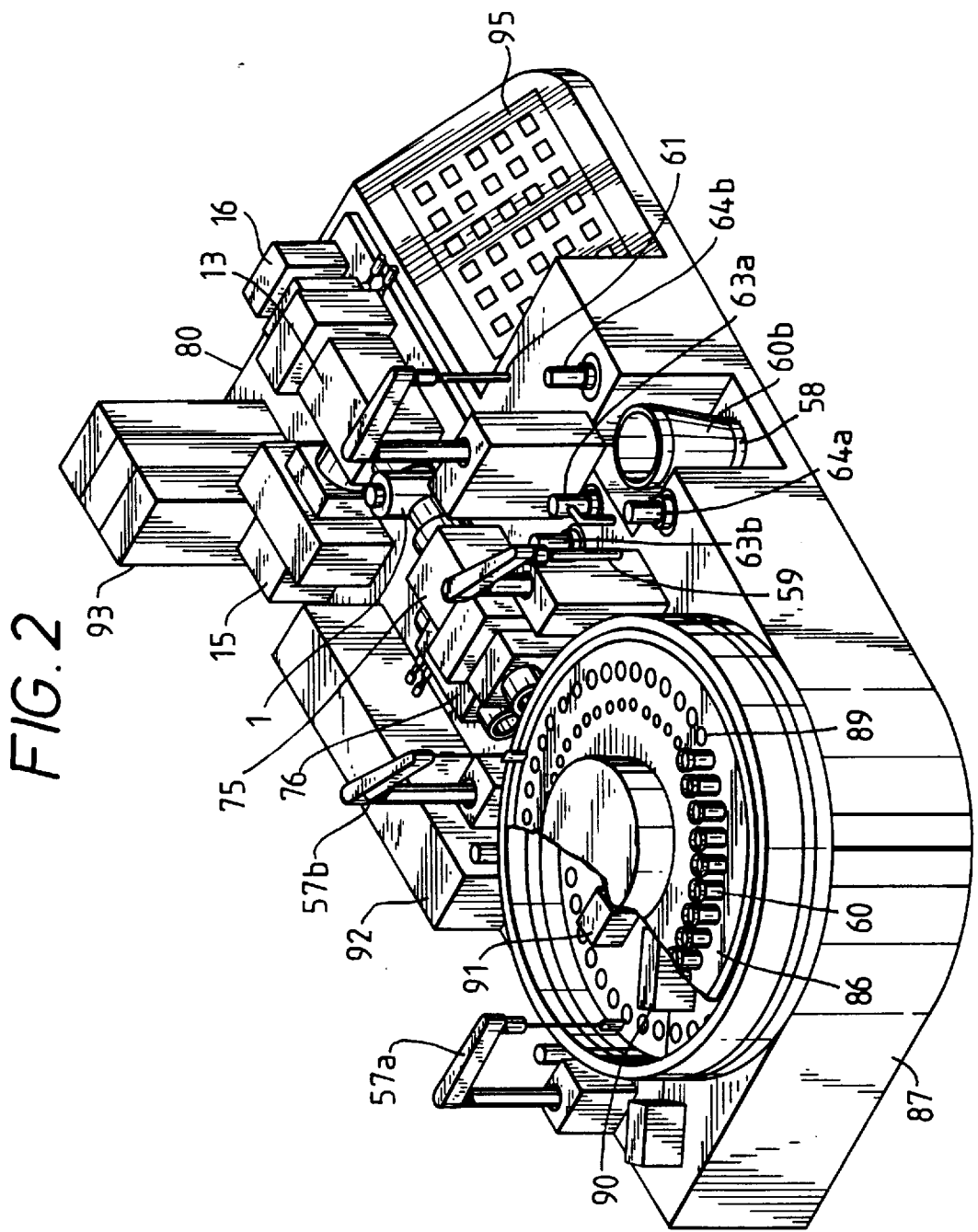
FIG. 2 is a perspective view of part of the apparatus of FIG. 1.

As shown in FIG. 1, the apparatus has: an optical measurement system 80, a processing unit 37, a display unit 38, and a keyboard 71 which are placed on the top of a table 94. A preprocessor 87 is placed next to the optical measurement system 80. Controllers 31, a drainage tank 81, a clean liquid bottle 82, a dyeing liquid bottle 83, and a washing liquid bottle 84 are located under the table top 94. The preprocessor 87 has a protective cover 85. The cover may be opened to mount or remove a sample disk 86. The display unit 38 is used to display the operating status of the device and results of analysis, and is located near the optical measurement system 80 so that the operator can work and, at the same time, monitor the operation status of the device and the results of analysis. The table top 94 has a space on which the operator can place the sample disk 86 and put specimens in the sample disk. An electromagnetic valve unit and a liquid supplier 93 are located behind the optical measurement system 80. There is also an operation panel 95 on the front of the optical measurement system 80.

The controllers 31 under the table top 94 are mounted on a slidable rack for easy maintenance. The drainage tank 81, the clean liquid bottle 82, the dyeing liquid bottle 83, and the washing liquid bottle 84 are provided on the front of the device so that they may be demounted easily for replacement.

As described above, and shown in more detail in FIG. 2, the preprocessor 87 is placed close to the optical measurement system 80. The preprocessor 87 has a removable sample disk 86 which has a series of one test tube holes 89 around its outer circumference. An absorbance sensor 90 and a bar code reader 91 to read bar codes attached to the sample containers are provided under the sample disk 86. A sampling pipet 59, a flow cell pipet 61, and stirrers 57a and 57b are provided around the periphery of the sample disk. These pipets 59 and 61 and stirrers 57a and 57b are designed to turn and move up and down. The sampling disk 86, a washing port 64a, and reaction tanks 63a and 63b all within the range of movement of the sampling pipet 59. Similarly, a flow cell 1, a washing port 64b, and reaction tanks 63a and 63b are all within the range of movement of the flow cell pipet 61.

Figure 3:
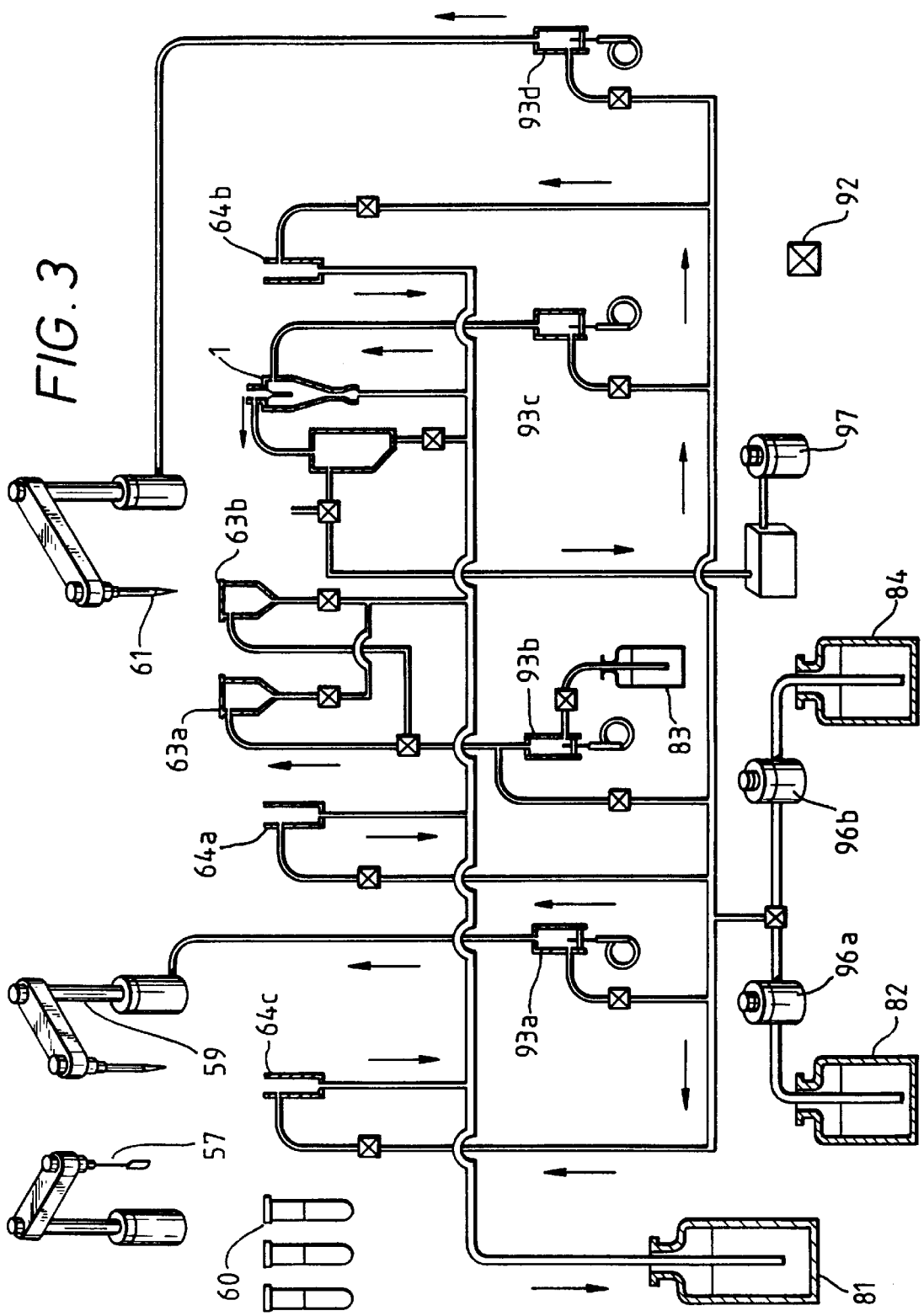
FIG. 3 is a perspective view of a piping system for the apparatus of FIG. 1.

FIG. 3 is a schematic representation of the piping system for liquids in this first embodiment of the present invention. The clean liquid bottle 82 stores clean liquid, which is free of particles of a size equal to or larger than those which may be found in any specimen. The clean liquid bottle is connected to the washing ports 64a and 64b, the reaction tanks 63a and 63b, the sampling pipet 59, and the flow cell pipet 61 through a liquid supply pump 96a, liquid suppliers 93a to 93d. Electromagnetic valves 92 are also provided in the piping system.

The dyeing liquid bottle 83 stores a reagent which quickly reacts with and dyes particles in specimens and is connected to reaction tanks 63a and 63b via the liquid supplier 93b. The washing liquid bottle 84 stores a liquid containing ingredients for cleaning the piping system and is connected to the piping system via the liquid supply pump 96b. The drain tank 81 is connected to the washing ports 64a, 64b, and 64c, the reaction tanks 63a and 63b, and the flow cell 1.

The operations of the liquid suppliers, electromagnetic valves, pumps, and pipets are all controlled by the controller 31. Liquid suppliers 93a and 93d are driven at a constant speed repeatedly to receive and expel a preset amount of liquid. This causes the sampling pipet 59 and the flow cell pipet 61 to receive and expel preset amounts of liquid at a precisely preset speed.

Figure 4:
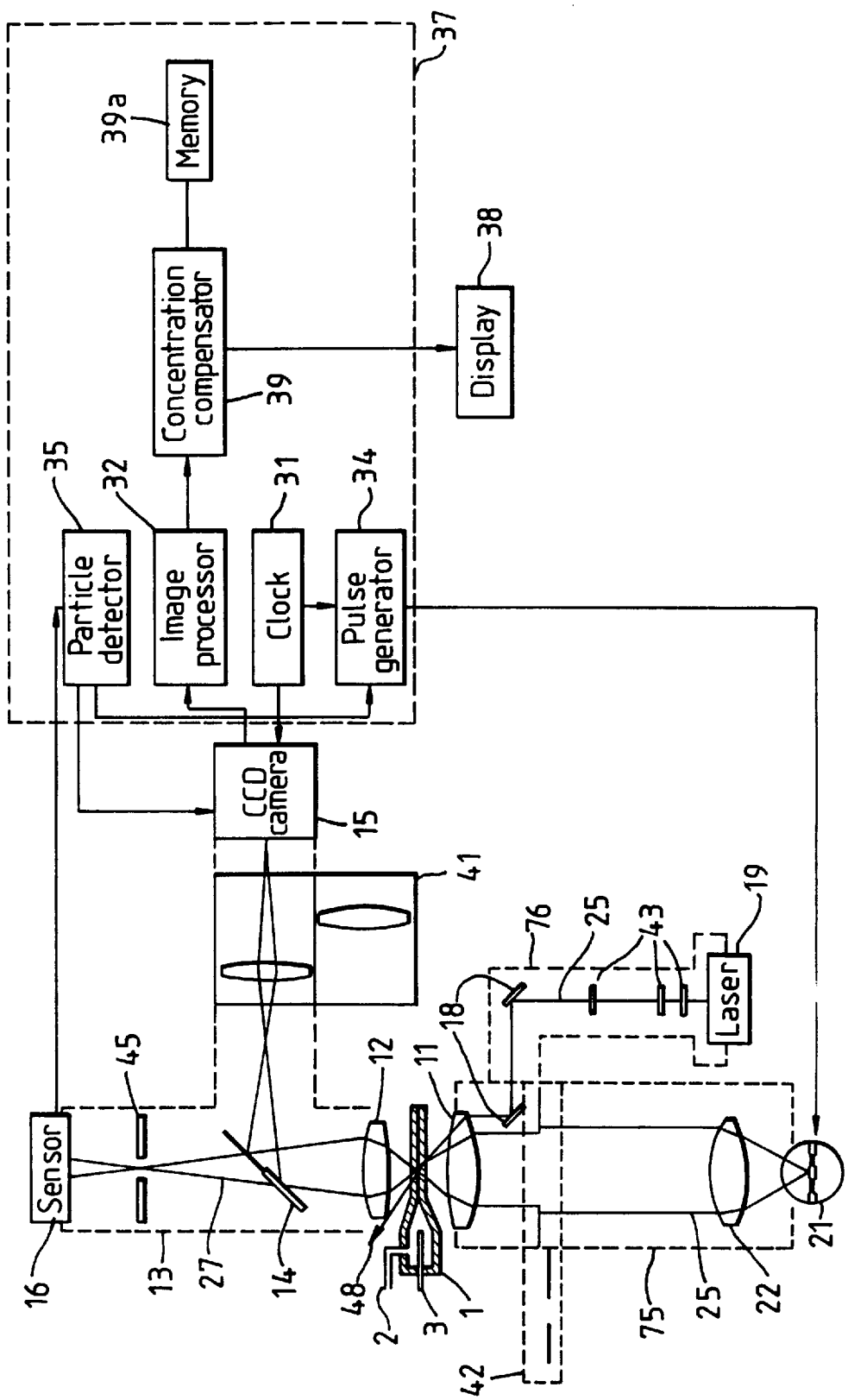
FIG. 4 illustrates the basic configuration of the detection system in the embodiment of FIG. 1.

The configuration of the detection system of this embodiment is illustrated in FIGS. 4 to 6. The upper and lower sides of the flow passage of the flow cell 1 are made of flat and clear glass and the flow cell is placed under the microscope 13 so that its flow passage may be at the focus of a microscope.

The flow cell has a sample liquid inlet 3 and a sheath liquid inlet 2 which encloses the sample liquid inlet 3 at the center of the upstream end of the flow cell 1. The sample liquid 6, which contains particles to be analyzed, is fed at a constant rate through the sample liquid inlet 3 and clean liquid containing no detectables particle is fed at a constant rate through the sheath liquid inlet 2. A steady laminar flow (sheath flow) is formed inside the flow cell 1 in which the sheath liquid encloses the sample liquid. The particles to be analyzed in the laminar flow are carried at a constant speed through the flow cell 1. In this laminar flow, the sample liquid flows in the form of a flat, thin and wide ribbon. The sample liquid supplying means and the sheath liquid supplying means have their liquid supply rates controlled so that the cross-sectional shape and the flow rate of the sample liquid 6 inside the flow cell 1 may be varied.

On one side of the flow cell, a light pulse emission system 75 and a laser light emission system 76 are provided, which illuminate the flow cell. A microscope 13 is provided on the other side of the flow cell 1. FIG. 4 illustrates optical systems in the light pulse emission system 75, the laser light emission system 76, and the microscope 13. The flow cell 1, the microscope 13, the light pulse emission system 75, and the laser light emission system 76 respectively have a movement mechanism for accurately adjusting their positional relationship.

The light pulse emission system 75 comprises a pulse light source 21, a lens 22, a variable diaphragm 42, and a condenser lens 11. The laser light emission system 76 comprises a laser 19, a conversion lens 43, a mirror 18. The condenser lens 11 is common to the laser light emission system 76 the light pulse emission system. The microscope 13 on the other side of the flow cell 1 comprises an objective lens 12, a semi-transparent mirror 14 behind the objective lens 12, a variable slit 45 and a sensor 16 on the transmission side, a variable lens 41 and a CCD camera 15 on the reflection side, and a beam trap 48 close to the objective lens 12.

As shown in FIG. 4, the image processor 32 is connected to the CCD camera 15 and the particle detector 35 is connected to a sensor 16. A signal representing the magnitude of light detected by the sensor 16 is sent to the particle detector 35. The particle detector 35 is connected to a counter 36 and to a pulse generator 34. The image processor 32 and the counter 36 are connected to a display unit 38 through a concentration compensator 39. A clock 31 is connected to the CCD camera 15 and to the pulse generator 34. The pulse generator 34 is further connected to a light pulse source 21 and to the concentration compensator 39.

Continuous light emitted from the laser 19 is trapped by a beam trap 48 and does not enter the objective lens 12. However, the light scattered by a particle moving in the flow cell 1 enters the objective lens 12, passes through the semi-transparent mirror 14, and then is detected by the sensor 16. The variable slit 45 in front of the sensor 16 allows light coming from a specific detection area in the flow cell 1 to pass through and shuts off all light coming from other areas.

The apparatus of this first embodiment of present invention has two magnification modes: High Magnification mode and Low Magnification mode. Switching between these modes is achieved by simultaneously changing the variable lens 41, the variable diaphragm 42, and the variable slit 45. Since the size of the area 9 to be illuminated by light pulses and the intensity of the light changes when the variable diaphragm 42 is changed, the CCD camera 15 can be set to optimum light intensity and contrast even when the magnification is changed. The variable slit 45 limits the range over which scattered light 27 can enter the sensor 16. When the width of this variable slit 45 is changed, there is a change in the range of the scattered light 27 to be detected by the sensor 16. When the magnification is changed, the width of the image pickup area varies and at the same time there is a change in the width of the area over which the scattered light is detected.

FIG. 6 illustrates the image pickup area and the detection area in the flow cell 1. Light from the image pickup area 10a is focussed by the objective lens 12 when the optical system is in the High Multiplication mode, reflected by the half-mirror 14, converted by the conversion lens 41, and picked up by the CCD camera 15. The image pickup area 10b is the area whose image is detected by the CCD camera 15 when the optical system is in the Low Multiplication mode. These areas are thin, flat and wide, like a tape. In each mode, the light from the light source 21 uniformly illuminates the corresponding image pickup area 10a, 10b. In the High Multiplication mode, light scattered by a particle in the detection area 50a is detected by the sensor 16. In the Low Multiplication mode, light scattered by a particle in the detection area 50b is detected by the sensor 16. Those detection areas 50a and 50b are upstream (to the direction of liquid flow) of the image pickup areas 10a and 10b. The length of a side of the detection area 50a, 50b to the direction of liquid flow is very small and the length of a side transverse to the direction of liquid flow is approximately equal to the width of a side of the corresponding image-pickup area 10a, 10b transverse to the direction of liquid flow. Continuous light from the laser 19 evenly illuminates a region including the detection areas 50a and 50b.

As described above, the width, thickness, and flow rate of the sample liquid flow in the flow cell may be changed in dependence on the multiplication mode. The liquid suppliers 93a and 93b controlled so as to supply the sheath liquid 5 and the sample liquid 6 at a constant rate so that the sample liquid may flow with a predetermined flow rate and with a predetermined width and thickness, depending on the multiplication mode. The width, thickness, and flow rate of the sample liquid flow are determined as follows:

i) In the High Multiplication mode, the thickness of the sample liquid flow is controlled to be approximately equal to or slightly less than the transverse width of the image-pickup area 10*a* determined by the microscope 13. Thus, in this mode, the sample liquid flows through a section a little narrower than the image pickup area 10*a*. The flow rate of the sample liquid is controlled so that the sample liquid may cover the image pickup area 10*a* (along the flow) in a much shorter time than the image pickup cycle period of the CCD camera (preferably at least 30 times the cycle period). The amount of the sample liquid flowing in the pulse direction of the pulse light source 21 is preferably smaller than the image resolution.

ii) In the Low Multiplication mode, the thickness of the sample liquid is controlled to be approximately equal to or slightly less than the thickness of the image pickup area 10*b* determined by the microscope 13. Thus, in this mode, the liquid sample flows through a section a little narrower than the width of the image pickup area 10*b*. Again, the flow rate of the sample liquid is controlled so that the sample liquid may cover the image pickup area 10*b* (along the flow) in a much shorter time than the image pickup cycle period of the CCD camera (preferably at least 30 times of the cycle period). The amount of the sample liquid flowing in the pulse duration of the pulse light source 21 is preferable smaller than the image resolution.

The operations of this embodiment of a particle analyzing device according to the present invention will now be described. The particle analyzing device of this invention has six operation modes: Setting, Waiting, Measurement, End, Emergency Test, and Holiday modes.

Firstly, the operation in the Setting mode will be described. The main switch is turned on and the "SETTING MODE" is selected using the operation panel 95. The display unit 38 shows the remaining amounts of liquids (reagent, clean liquid, washing liquid, etc.). A check is made that the amount of each liquid left available is sufficient. If the amount of any liquid is not sufficient, the corresponding bottle needs to be replaced by a new one. Also, the quantity of drainage in the drainage tank 81 needs to be checked, using the display screen. If it is full, the drainage tank needs to be emptied.

Before entering the Measurement mode, the operator puts sample liquid in sample containers 60 and attaches a bar code label containing sample information to each container 60. The sample containers 60 are put in the sample disk 86, which can have many sample containers 60 therein. Then the sample disk 86, having the sample containers 60, is mounted in the preprocessor 87. The operator can put another sample liquid on another sample disk 86 for the next analysis while the analyzing device 71 is in service.

If the "MEASUREMENT MODE" is selected using the operation panel 95, and the START button pressed, the analyzing device 72 works automatically until it has analyzed all specimens set on the sample disk 86. Before the analysis starts, the analyzing device causes the sample disk 86 to make a full revolution, reads the bar codes of all sample containers on the sample disk, and stores their specimen numbers in a memory. When the analysis starts, the display unit 38 shows the specimen number of a currently-analyzed sample container and the number of specimens to be analyzed which are on the sample disk 86. After analyzing the last sample on the sample disk, the analyzing device 72 automatically stops measurement and enters the Waiting mode. When the sample disk 86 is replaced by another sample disk having new specimens on it, the analyzing device automatically re-enters the Measurement mode and analyzes the new specimens.

If the EMERGENCY TEST button on the operation panel 95 is pressed while the analyzing device is in the Measurement or Waiting mode, the analyzing device temporarily stops analyzing sample liquid in the current sample container on the sample disk 86 and enters the Emergency Test mode in which a specimen requiring an urgent analysis can be processed. When a sample container 60*b* of a specimen which requires urgent analysis is placed on the secondary sample stand 58, the sampling pipet 59 sucks in the sample liquid and transfers it for analysis. In this Emergency Test mode, a desired number of specimens can be analyzed preferentially. At the end of the urgent analysis, the analyzing device returns to the mode in which it had been operating set before the Emergency Test mode.

After analyzing all specimens for a day, the End mode is set. Also in this mode, the display unit 38 shows the remaining amount of liquids (dyeing liquid, clean liquid, washing liquid, etc.). The amount of each liquid left available should then be checked. If the amount of any liquid is not sufficient, the corresponding bottle needs to be replaced by a new one. The pipets, the reaction tank, and the piping system should be washed with the washing liquid, a list of the analysis results displayed and printed out, then the main switch can be turned off.

If the particle analyzing device is not to be used for a long time, the Holiday mode can be set. In the Holiday mode, although the particle analyzing device is not in service, it flushes the flow paths in the piping system and the flow cell once a day with clean liquid to prevent the piping system and the flow cell from being stained, clogged, becoming dry. It is also possible to enter a calendar of holidays in advance in the particle analyzing device. When a fault is detected on a holiday, the particle analyzing device may automatically inform an appropriate maintenance service.

In the Measurement mode, a sample disk 86 having sample containers with bar code labels on it is put in the preprocessor 87. When the sample disk 86 is received, the preprocessor 87 turns the sample disk 86 and causes the bar code reader 91 to read the bar code of each sample container 60 on the sample disk. The read data (presence or existence of a sample, sample type, and specimen number) is used as process data and for identification. An absorbance sensor 90 is provided to measure the absorbance of each samples and detect abnormal samples before analysis.

After being stirred by the stirrer 57*b*, the sample container 60 on the sample disk is moved and stopped in the moving area of the sampling pipet 59. After stirring sample liquid in a sample container 60, the tip of the stirrer 57*b* is washed in the washing port 64*c*. The tip of the sampling pipet 59 is put into a sample container 60, the contents, extracted and the sampling pipet 59 then moves to one of the reaction tanks 63*a* and 63*b* together with the sample liquid. A preset amount of the sample liquid is then put into the reaction tank 63*a*, 63*b*. Suction and ejection of sample liquid into and out of the pipet 59 is achieved by controlling the amount of movement of a piston of the liquid supplier 93*a*. After the sample liquid has been ejected into the reaction tank, the end of the sampling pipet 59 is put into the washing port 64, to wash it. During the washing period, clean liquid is supplied from the clean liquid bottle 82 to the washing port 64 to flush clean the sampling pipet 59.

After this, the liquid supplier 93*b* is driven to transfer a preset amount of the dyeing liquid from the dyeing liquid bottle 83 to the selected reaction tank 63*a* or 63*b*. The sample liquid and the dyeing liquid are stirred and mixed for a preset time in the reaction tank. Then the flow cell pipet 61 is inserted into the reaction tank 63 and the dyed sample is extracted. After this, the reaction tank 63 is washed clean with clean liquid. The liquid used to wash the tank is drained to the drainage tank 81.

The flow cell pipet 61 holding the dyed sample moves to the flow cell 1 and its tip is inserted into the top of the flow cell 1. When the tip of the flow cell pipet 61, is received by the flow cell, the inlet of the flow cell 1 closes tightly. The liquid supplier 93a starts to supply clean liquid from the clean liquid bottle 82 to the flow cell 1 and then the liquid supplier 93 causes the flow cell pipet 61 to inject the dyed sample liquid into the flow cell. The supply of the clean liquid and the injection of the dyed sample liquid are controlled by the liquid suppliers 93c and 93d so that they may be a preset flow rate may be achieved. As described above, the liquids pass as a laminar flow through the flow cell towards the drainage tank 81. The particle analyzing device waits until the flow inside the flow cell 1 is steady and then starts measurement.

The analyzing device first starts measurement in the Low Magnification mode. After a preset time, the supply of the sample liquid and the clean liquid is slowed to a slower rate for a preset time. Simultaneously when the supply speeds are changed, the variable lens 41, the variable slit 45, and the variable diaphragm 42 are changed to correspond to the High Magnification mode. The measurements on the sample are repeated in the High Magnification mode for a preset time. After all the contents of the flow cell pipet 61 have been injected, the flow cell pipet 61 is washed in the washing port 64b.

Before the analysis of one specimen is completed, the particle analyzing device starts another measurement by turning the sample disk 86, causing the sampling pipet 59 to suck in the next specimen, putting the sample liquid in the other reaction tank 63a or 63b, and mixing it with the dyeing liquid by the stirrer. When washing of the flow cell pipet 61 used for the current specimen is completed, mixing of the next specimen with the dyeing liquid has already been completed and is ready for the next analysis. Thus these reaction tanks 63a and 63b are used alternately to permit continuous analysis.

In the Emergency Test mode, it is also possible to put a specimen on the secondary sample stand 58 for urgent analysis. In this case, the sample disk 86 is not used. Sample liquid is put in a sample container 60b and placed on the secondary sample stand 58. The sampling pipet 59 extracts sample liquid directly from the sample container 60b and transfers it to the reaction tank 63 for analysis.

FIG. 7 illustrates the timing of the image pickup system during a measurement operation. The CCD camera 15 may be of the interlace type and may thus synthesize two field images into a single screen image. The image storage period of field S deviates from that of field T by a field cycle (half of a frame cycle). Each field has an image storage period and an image transfer period in a frame, to form a single image.

The CCD camera stores the amount of light incident upon the image pickup plane as an electric charge in a memory during the image storage time and transfers the stored electric charge in a comparatively short time during the transfer period. No electric charge remains after it is transferred. Then the storage period re-starts.

The sensor 16 in FIG. 4 receives light scattered by a particle and sends a signal representing its intensity to the particle detector 35. When a particle 7 to be analyzed moves through the detection areas 50a or 50b in the flow cell 1, the intensity of light incident upon the sensor 16 varies. The particle detector 35 detects when there is a change of at least as great as a preset level and classifies the change in the signal into an appropriate signal class in dependence on preset patterns. When the change in the signal change belongs to any of the preset signal classes, the particle detector outputs a timing signal. The or each signal class which causes a timing signal to be generated are specific to each magnification mode.

The pulse generator 34 has a gate circuit. The gate signal operates in the same cycle as the field cycle of the CCD camera 15. The gate closes a suitable delay time before either of the fields, enters a transfer period, and opens after the transfer period. If a timing signal is received when the gate signal is "open", a Flash On signal is generated after a predetermined delay time which is equivalent to the time in which a particle 7 to be analyzed moves from the area 8 illuminated by continuous laser light to the image pickup area 10a, 10b in the flow cell 1. The pulse light source 21 flashes due to this Flash On signal. The delay time is specific to each magnification mode. The gate remains closed until the next field cycle starts and opens again when the image storage period of the next field cycle starts. A Flash On signal is not generated when a timing signal is input while the gate signal is at "close". In other words, the pulse light source 21 is designed to flash only once in two consecutive field cycles of the CCD camera 15.

The CCD camera 15 takes an image of a particle 7 which is moving in the image pickup area 10a, 10b when the pulse light source flashes, the image is then stored as an electric charge, and the charge is transferred to the image processor 32. The image processor 32 analyzes the image data and classifies it into a shape class according to the type and properties of the particle 7.

When the image contains two or more particles, each particle is analyzed. The image processor 32 outputs the result of the analysis to a concentration compensator 39. At the end of a series of measurements, the concentration compensator 39 calculates the concentration (density) of particles in the specimen according to the number of the photographed particles and outputs the result to the display unit to display. The particle concentration is calculated as follows:

The relationship between the concentration of particles in a specimen and the number of photographed particles is obtained as follows:

The mean number of particles contained in a sample volume equivalent to one image-pickup field is determined by Equation 1.

$$\lambda = nv \qquad \text{Equation 1}$$

The expected number of photographed particles $N_t$ is determined by Equation 2.

$$N_t = N_f P_f n_f \qquad \text{Equation 2}$$

In these Equations 1 and 2 $N_f$ is a field number determined by the field cycle and the time of measurement of the CCD camera. It is constant when the conditions of measurement are determined. The photograph probability of a field represents the probability of a particle being present and photographed in the field during a field cycle (while the gate is open). This value increases with increase in concentration (density), and decreases with decrease in concentration. In Equation 2, $N_f$ is the predicted number, for particles in one image, of the number of particles in a screen which are detected and photographed. This value is approximately when the particle concentration is large and approximately 1 when the particle concentration is small. For the embodiment of the particle analyzing device of the present invention, values of $N_f$, $P_f$, and $n_f$ are approximately 3, 4, and 5 respectively.

The following equations hold $$N_f = \frac{T}{t_f} \qquad \text{Equation 3}$$

$$P_f = \frac{1 - e^{-m\lambda}}{2 - e^{-m\lambda}} \qquad \text{Equation 4}$$

$$n_f = e^{-(1-h)\lambda} + \lambda \qquad \text{Equation 5}$$

In Equations 3 to 5, T is the time of measurement, $t_f$ is a field cycle, m is an acceleration determined by the flow conditions, h is a constant determined by the conditions of the photographing of the image.

The acceleration m is Equation 6.

$$m = \frac{V_f}{v} \frac{(t_f - t_t)}{t_f} \qquad \text{Equation 6}$$

In Equation 6, $V_f$ is the volume of sample liquid flowing in a field cycle. It is the product of the cross section of the view field through which the sample liquid flows, the flow rate of the sample liquid and the field cycle time. v is the volume of liquid in the view field, which is, the product of the cross section of the view field and the length of the view field in the direction of liquid flow. The value of m increase with increasing flow rate of the sample liquid becomes greater. As seen from FIG. 4, the value of $P_f$ increases as the value of m increases greater. Therefore, a greater flow rate will increase the number of photographed particles. Furthermore, the value of m increases with decreasing transfer time $t_t$ of the CCD camera.

From Equations 1 to 6, the relationship between the number of photographed particles $N_t$ and the particle concentration n can be obtained. This is applicable to any particle concentration (from low concentration to high concentration).

When the magnification mode is changed, the volume of view field v changes. Therefore, the acceleration rate m should be unique to each magnification mode, to change the flow rate of the sample liquid. Similarly, the time of measurement T should also be unique to each magnification mode. The constant h is a unique value which is determined according to the operating conditions. As will be described in more detail later, the selection of the magnification mode may be in dependence on the type or number of particle present, therefore the particle detector 35 may generate an output to the CCD camera, as shown in FIG. 4.

The concentration compensator 39 stores the relationship between the particle concentration and the number of photographed particles in a memory 39a. When it receives a signal corresponding to a number of particles photographed, the concentration compensator 39 converts the signal into a particle concentration and outputs the result.

Figure 9:
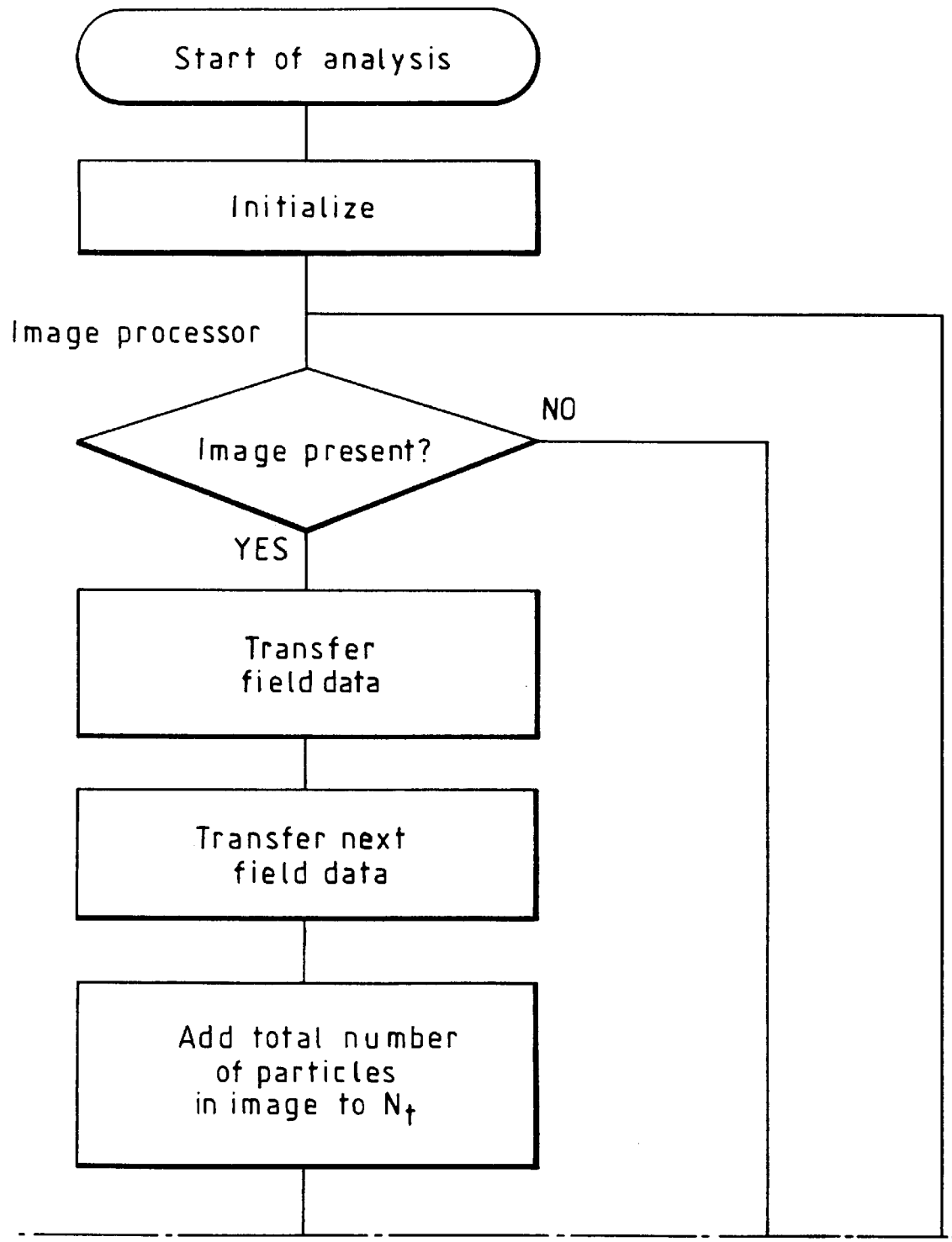
FIG. 9 is a flow-chart illustrating concentration analysis in the embodiment of FIG. 1.

FIG. 9 shows the operational flow of analysis to particle concentration (density). First there is analysis of a specimen which, as has previously been described, involves resetting internal data of the image processor 32 and the concentration compensator 39, initializing, entering a measurement period, determining whether or not an image was taken in each field cycle, outputting the field data of the CCD camera 15 when no image was taken and entering the next field cycle directly or transferring data of two fields of the CCD camera 15 to the image processor 32 when images were taken, causing the image processor 32 to synthesize image data of two fields into a single static image, analyzing the static image to get the total number of particles in the image, classifying particles by shapes (into shape classes), adding the obtained total number of particles to $N_t$, and adding the number of particles belonging to shape class j to $P_j$. As image determination is performed once every two field cycles, this process is performed within a time equivalent to two field cycles.

The steps described above are repeated until the end of the measurement time. At the end of the measurement time, the concentration compensator 39 calculates a particle concentration from $N_t$ using the relationship between the number of particles photographed and particle concentration i.e. modifies the initial particle concentration determined from the number of particles photographed. The concentration compensator 39 calculates the ratio of particles ($P_j$) belonging to each shape class (j), multiplies it by its concentration, and records the result as the concentration of each particle type.

Figure 8:
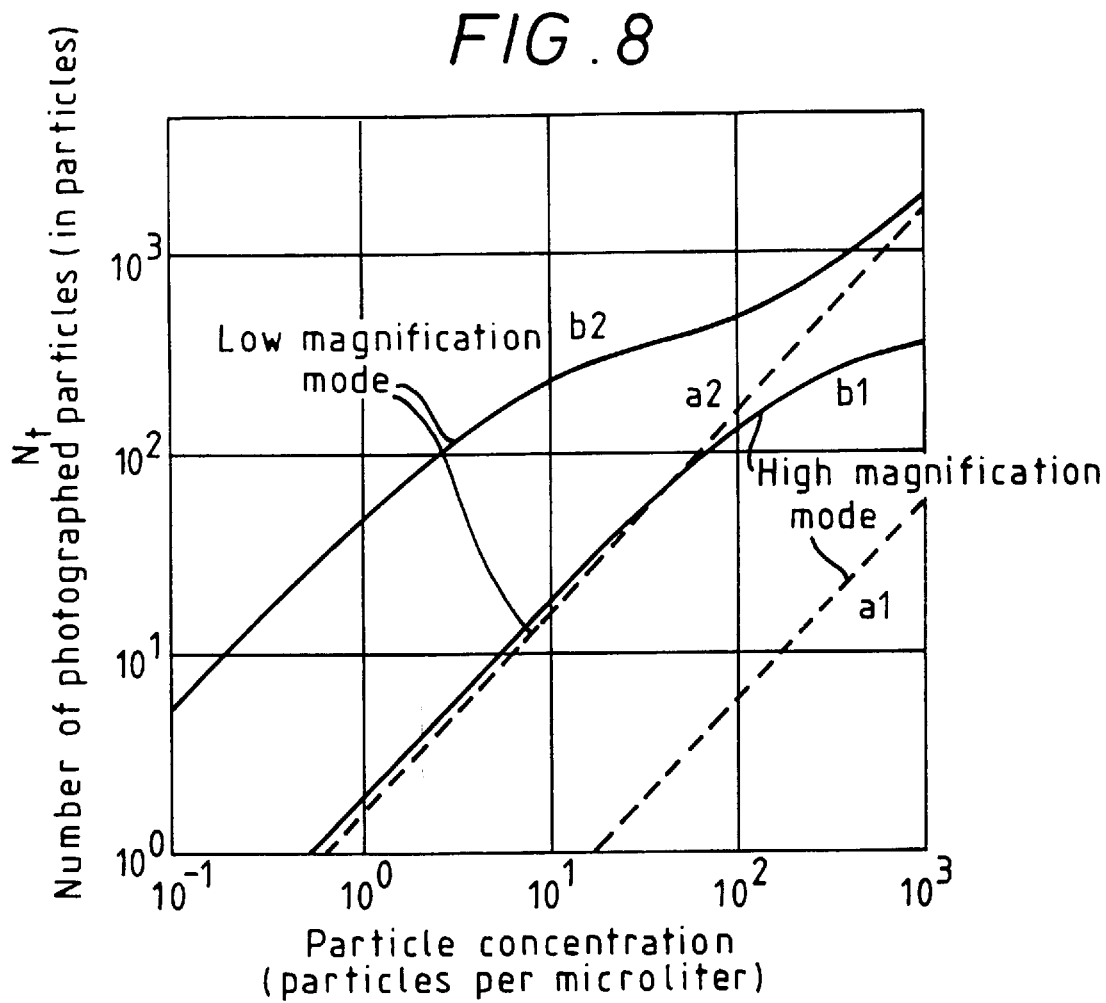
FIG. 8 is a graph showing the relationship between particle concentration and number of particles photographed.

A series of such measurements are performed in both Low and High Magnification modes under different conditions. FIG. 8 illustrates examples in which the relationship between the concentration of particles in a specimen and the number of particles photographed is calculated. The X axis of the graph represents concentration of particles in the specimen and the Y axis represents the expected total number of photographed particles. The dotted lines a1 and a2 show the relationship between the number of particles photographed and the particle concentration in each magnification mode when the CCD camera was driven periodically only even when no particle is detected. The solid lines b1 and b2 plot the relationship between the number of particles photographed and the particle concentration in each magnification mode for one embodiment of the present invention. As the High Magnification mode and the Low Magnification mode have different conditions of measurement, constants specific to each magnification mode are used for the calculations.

In this embodiment, the sample liquid flows at a high flow rate through a section whose width (transverse to the flow) is a little narrower than but approximately equal to the width of the image pickup area. In other words, a large quantity of sample liquid can flow through the image pickup area 10a or 10b. Accordingly, the acceleration rate m shown in Equation 6 is large and a large number of particles can be analyzed.

As seen from FIG. 8, when the particle concentration range is low, this embodiment can photograph many more particles (more than 30 times) than when the present invention is not used (a1 and a2). For lines a1 and a2, the number of particles that are photographed is too small to be analyzed and classified into shape classes. For lines of b1 and b2, on the other hand, the number of particles that are photographed is sufficient for analysis and good information concerning the particle shapes can be obtained.

If the number of particles photographed is small, it may be hard to estimate the particle concentration from the number of particles photographed.

Since the accuracy of the determination of the particle concentration increases with the number of particles photographed, this embodiment is capable of photographing many more particles (30 times or more). This gives a highly accurate estimation of particle concentrations and also enables estimation of particle concentrations of very diluted samples (30 times or more).

If a sample has a large particle concentration, the number of particles photographed does not increase so much, but the photography of some hundreds of particles is enough for accurate particle analysis by shapes and estimation of particle concentration. To get results as accurate as those achieved by this embodiment, a conventional arrangement would have to prolong the time of measurement by 30 times or more. This embodiment has the effect of shortening the measurement time.

Furthermore, in this embodiment, since the distance that a particle moves at a given flow rate while the pulse light source 21 flashes is smaller than the image pickup resolution of the CCD camera, the particle is almost still and clear in the image so that it can be analyzed satisfactorily. Even when the sample has a low particle concentration and only particles that passes intermittently can be photographed, the possibility of photographing particles is increased (as illustrated by Equation 2) and an accurate relationship between the measurements in images and particle concentration can be obtained (from Equation 2). Hence, an accurate particle concentration can be obtained from the number of particles photographed.

Similarly, even when a sample has so many particles that all of the particles passing through the view field cannot be photographed, Equation 2 can offer an accurate non-linear relationship between the particle concentration and the measurements on the images. Furthermore, when the sample contains many more particles and one view field contains several particles, Equation 3 can be used to give an accurate relationship between particle concentration and the number of particles in a single image. Thus, in said case an accurate particle concentration can be obtained from the number of particles photographed.

As described above, this embodiment can give accurate particle concentrations even a wide range of particle concentrations in specimens (from low concentration to high concentration). Since this embodiment calculates a particle concentration only from the number of particles photographed, it can give an accurate concentration of target particles from the number of photographed particles even when the sample contains one or more other kinds of particles or when particles cannot be detected and counted accurately.

Furthermore, this embodiment controls the supply rate of sample liquid and the supply rate of clean liquid accurately, using liquid suppliers 93c and 93d. The time of measurement is also controlled by the controller 31. Hence a stable laminar flow (sheath flow) is formed in the flow cell 1. With this control, the quantity of sample liquid passing through the area 8 illuminated by continuous laser light and the image pickup area 10 and 10b during the time of measurement is always stable and constant. The quantities of sample liquid and dyeing liquid passed to the reaction tank 63 are accurately regulated by controlling the movement of the liquid suppliers 93a and 93b. Accordingly, the dilution of the sample liquid by the dyeing liquid can be calculated accurately.

In the flow cell 1, the sample liquid 6 has a flow in the form similar to a flat and thin tape whose thickness is approximately equal to that of the image pickup area and whose width across the flow is equal to or a little narrower that the width of the image pickup area. In such a flow cell, every particle in the sample liquid moves through the focus of the camera optical system and can be photographed sharply, which enables satisfactory image analysis. As all sample liquid fed to the flow cell 1 moves through the image pickup area, the quantity of sample liquid fed to the flow cell is equal to the quantity of sample liquid to be analyzed. Accordingly, the operator can easily and accurately determine the amount of the analyzed sample liquid and the rate of dilution (by the dyeing liquid). Thus the particle concentration of the sample can be calculating accurately.

Furthermore this embodiment stirs sample liquid, by use of the stirrer 57, just before starting the analysis so that any sediment in the sample may be dispersed uniformly before measurements are made. This makes analysis of particle concentration more accurate. This embodiment has two pipets: a pipet to transfer sample liquid from a sample container 60 to the reaction tank 63 and a pipet to transfer sample liquid from the reaction tank 63 to the flow cell 1. These two pipets enable analysis of many specimens in a short time (since a subsequent sample can be dyed while the current sample is being measured). Since both the sampling pipet 59 and the flow cell pipet 61 suck in sample liquid only at their tips and the piping system is substantially uncontaminated by sample liquid, the time required to wash out sample liquid left in the piping system can be significantly reduced. Therefore, many specimens can be analyzed in a short time. Additionally, this effectively eliminates contamination by the current sample liquid of the next specimen and reduces the amount of washing liquid that is needed.

Furthermore, in this embodiment, the flow cell pipet 61 injects sample liquid directly into the flow cell 1. The sample liquid is immediately formed into a steady laminar flow without passing through a long pipe, and measured and analyzed without a time delay. This enables quick analysis of a lot of specimens in a short time.

This embodiment has more than one reaction tank 63 which are used alternately and efficiently to analyze a lot of specimens in a short time. For example, while one tank is being used to mix up the sample liquid with the dyeing liquid, the other tank may be washed and made ready for the next specimen.

In this embodiment, the upper and lower sides of the flow cell are flat and transparent and the sample liquid 6 flows with even thickness and width and at constant flow rate from the detection area 50a and 50b to the image pickup area 10a and 10b in the flow cell 1. In any part of the flow cell, particles are detected and photographed under constant conditions. This enables effective use of the view fields, efficient analysis of the sample liquid, and exact evaluation of the volume of the view field. This also makes analysis of particle concentrations more accurate.

The width (across the flow) of a flow of sample liquid is a little narrower than the width of the image pickup area 10a, 10b, which is as wide as the detection area 50a, 50b. Hence almost all the particles in the sample liquid 6 will pass through the detection area 50a, 50b and the image pickup area 10a, 10b. All particles are detected without omission. Additionally, since a detected particle is photographed after a preset delay time, it is always photographed at a constant position in the image pickup area 10, which prevents particles from being clipped in the image. The fact that the images are of whole particles make image analysis easier.

Furthermore, this embodiment has an accurate movement mechanism on each of the flow cell 1, the microscope 13, the pulse light emission system 75, and the laser light emission system 76. These movement mechanisms enable the pulse light emission area 9 to be matched with the image pickup area 10a, 10b. The continuous light emission area 8 is matched with the detection area 50a, 50b. These areas are aligned with the center axis of the flow cell 1. Thus, when the flow cell 1 and the pulse light source 21 are replaced for maintenance, their light axes can be adjusted easily.

In this embodiment, the detection area 50a, 50b is upstream of the image pickup area 10a, 10b in the flow cell 1, the laser light emission system 76 has only to illuminate an area upstream of the image pickup area 10a, 10b, which prevents the laser light 9 from entering the CCD camera 15 and spoiling the images. Similarly, the pulse light emission system 75 has only to illuminate an area downstream of the particle detection area 50a, 50b, which prevents the light from the pulse light source 21 from entering the sensor 16 and influencing the particle detection.

In this embodiment, the detection area 50a, 50b is very narrow in the direction of the flow of liquid so that the timing of detection of a particle should not be affected by the position of the particle in the detection area. With this timing, a particle passing through the detection area may be photographed in the image pickup area 10a, 10b. The area 8 to be illuminated by the continuous laser light can also be narrow, so that the laser 19 can have a small output and the sensor 16 can be of the low sensitivity to get scattered light which is sufficient to be detected. This reduces the cost reduction of the device.

Since both the pulse light emission system 75 and the laser light emission system 76 use a common condenser lens 11 to illuminate the flow cell 1, the particle analyzing device can be made compact. Furthermore, these light emission systems may be structured so that they may be adjusted as a unit.

The particle analyzing device uses a common objective lens 12 to detect scattered light and for the CCD camera 15, for additional compactness. Furthermore, the two detection systems may be structured so that they may be adjusted as a unit. When the CCD camera 15 and the variable slit 45 are fixed to the microscope 13, the positional relationship of the detection area 50 and the image pickup area 10a, 10b is assured so that a particle detected in the detection area 50 can be photographed accurately in the image pickup area 10a, 10b. This makes the analysis more efficient.

It is also possible to place the area illuminated by the pulse light emission system 75 close to the area illuminated by the continuous light emission system, which eliminates any effects due to uneven flow rate distribution or change of flow rates in the flow cell during analysis.

This embodiment of the particle analyzing device employs a CCD camera 15 as an image pickup device. This CCD camera can photograph a particle which is flash-illuminated by the pulse light source 75 at the same time as it stores image data in a memory. With the use of the CCD camera 15, this embodiment can obtain static images of particles even without use of a high-speed shutter. This makes the particle analyzing device cheaper. The pulse light source 76 can generate very short intermittent illumination. Therefore, the flow rate of the sample liquid can be increased without making images faint. This increases the efficiency of particle analysis. Furthermore, the transfer period of the CCD camera will normally be shorter than the image storage period. Accordingly, the time which is not available for photographing is very short and consequently more particles can be photographed, as given by Equation 6. This increases the efficiency of particle analysis.

This embodiment needs no special modifications to the control of the operation of the camera since the CCD camera 15 is only operated cyclically. This embodiment uses only the standard functions of the CCD camera. The CCD camera may be of any particular type. It can be an inexpensive and ordinary CCD camera. This reduces the production cost of the particle analyzing device.

The image recording means may be an inexpensive and general-purpose recording medium such as a video tape recorder, since the CCD camera operates intermittently regardless of whether particles move through the flow cell intermittently or irregularly. Such a recording device enables later analysis and display of particle images.

This embodiment carries out only makes at most one photographing operation for two consecutive fields and the pulse light source 21 flashes at an interval not less than one field period. Therefore, the pulse light source 21 can be an inexpensive one whose flashing interval is comparatively long. The to a short flashing intervals and the stable intensity of illumination permit high quality images to be obtained.

This embodiment has two magnification modes (HIGH and LOW) and changes the image magnification, the size of the detection area, the size of the view field, and the flow rate of the sample liquid in dependence on the selected magnification mode. This effective use of the image pickup area in both magnification modes increases the efficiency of analysis. Furthermore, the delay time is varied in dependence on the selected magnification mode so that a particle may be photographed as soon as it moves into the image pickup area 10a, 10b in each magnification mode. This increases the efficiency of particle analysis. Since the coefficients of the formula relationship between particle concentration and number of photographed particles are varied according to the selected magnification mode, exact particle concentrations can be obtained in both magnification modes.

In this embodiment, the operator can know the concentration of target particles in the sample liquid from the output of the particle detector before an image analysis is performed and change the flow rate of the sample liquid so as to get the optimum number of particles for analysis. The sheath liquid is clean and free from any unwanted particles that may otherwise be detected and photographed.

A second embodiment of the present invention will now be described with reference to FIGS. 11a to 11d. FIGS. 11a to 11d illustrate four ways (a) to (d) in which a sample liquid may flow through the view field of the flow cell of the first embodiment of the present invention. In each way, the size of the detection area 50a, 50b, and/or the size of the image pickup area 10a, 10b and/or the flow rate of sample liquid are changed according to the magnification mode selected.

In way (a), shown in FIG. 11a the width of the flow 6a, 6b of sample liquid remains unchanged in both Low and High magnification modes, but the flow rate and the thickness of the flow are changed in dependence on the magnification mode selected. The width (across the flow) of the sample liquid flow 6a, 6b is made greater than the width of the image pickup area 10a, 10b in either magnification mode and the width of the detection area 50a, 50b is changed so as to be approximately equal to the width of the image pickup area 10a, 10b. Therefore, only part of the sample liquid fed to the flow cell 1 flows through the image pickup area 10a, 10b, particularly in the High Magnification Mode. However, an accurate determination of the volume of the sample liquid flowing through the image-pickup area 10a, 10b can be obtained by pre-determining the ratio of sample liquid passing through the image pickup area 10a, 10b to the volume supplied to the flow cell. The width of the image pickup area 10a, 10b and the width of the detection area 50a, 50b vary, but their widths are kept approximately identical. Therefore, a particle detected in the detection area 50a, 50b always passes through the image pickup area 10a, 10b. The width of the sample liquid flow 6a, 6b need not be adjusted accurately because only the flow rate and thickness of the sample liquid flow are controlled. Additionally, only the central part of the sample liquid flow needs to have a uniform flow rate and thickness since only the central part of the flow 6a, 6b is measured. This can simplify the structure of the flow cell 1. Furthermore, in either magnification mode, the sample liquid 6a, 6b flows with a uniform width at least equal to the width of the image pickup area 10a, 10b. This means that the image pickup area 10a, 10b is used efficiently and increases the efficiency of analysis. Furthermore, the flow passage can be made wide since the sample liquid flow 6a, 6b has a large width and hence particles will not become clogged in the flow passage.

In the way (b), shown in FIG. 11b, the width of the flow of sample liquid 6 remains unchanged in both Low and High Magnification modes, but the flow rate and the thickness of the flow are changed in dependence on the magnification mode selected. In the Low Magnification mode, the width (across the flow) of the sample liquid flow 6a is a little smaller than the width of the image pickup area 10a in the Low Magnification mode and the width of the detection area 50a, 50b is changed so as to be approximately equal to the width of the image pickup area 10a, 10b in either magnification mode. Therefore, in the High Magnification mode, only part of the sample liquid fed to the flow cell 1 flows through the image pickup area 10b. However, an accurate determination of volume of the sample liquid flowing through the image-pickup area 10b can be obtained by predetermining the ratio of sample liquid passing through the image pickup area 10b to the volume supplied to the flow cell. The width of the image pickup area 10b and the width of the detection area 50b are approximately identical. Hence, a particle detected in the detection area 50b always passes through the image pickup area 10b. In the Low Magnification mode, all the sample liquid supplied to the flow cell 1 passes through the image pickup area 10a, and thus the operator can know the volume of sample liquid passing the image pickup area more accurately. In the High Magnification mode in which the focal distance of the microscope is short, the images are sharp and even small particles can be analyzed accurately because only the central part of the sample liquid flow 66, which has a uniform flow rate and thickness is measured. The width of the sample liquid flow 6a, 6b need not be adjusted accurately because only the flow rate and thickness of the sample liquid flow are controlled. Accordingly, the flow cell 1 can have a simple structure. Additionally, in any magnification mode, the sample liquid flows uniformly keeping its width approximately equal to the width of the image pickup area 10a in the Low Magnification mode. This means that the image pickup area 10a, 10b is used efficiently and increases the efficiency of analysis.

In the way (c), shown in FIG. 11c, the width of the flow of sample liquid 6a, 6b remains unchanged in both Low and High Magnification modes, but the flow rate and the thickness of the flow are changed in dependence on the magnification mode selected. In the High Magnification mode, the width (across the flow) of the sample liquid flow 6b is a little wider than the width of the image pickup area 10b and the width of the detection area 50a, 50b remains unchanged. Therefore, in any Magnification mode, all sample liquid fed to the flow cell 1 flows through the image pickup area 10a, 10b. Hence, the operator can know accurately the volume of the sample liquid flowing through the image pickup area 10a, 10b. Also, the detection optical system is made simple as the width of the detection area 50a, 50b need not be changed. Consequently, the particle analyzing system can be made compact and the adjusting procedure can be simplified. The width of the sample liquid flow 6a, 6b need not b3 adjusted accurately because only the flow rate and thickness of the sample liquid flow 6a, 6b are controlled. Accordingly, the flow cell 1 can have a simple structure. In the High Magnification mode, the sample liquid flows uniformly, with a width approximately equal to the width of the image pickup area 10b. This means the image pickup area 10b is used efficiently and increases the efficiency of analysis. Also in the Low Magnification mode, the width of the sample liquid 6a is kept narrow and the sample liquid can flow steadily at higher flow rate. This increases the efficiency of analysis. Also in this mode, whole particles are photographed since particles will never move near the ends of the image pickup area 10. This makes image analysis accurate.

In the way (d), shown in FIG. 11d, the width, flow rate, and thickness of the flow of sample liquid 6 are changed in dependence on the Magnification mode selected. In either magnification mode, the width (across the flow) of the sample liquid flow 6a, 6b is made a little narrower than the width of the image pickup area 10, but the width of the detection area 50 remains unchanged. Hence, in either magnification mode, all sample liquid fed to the flow cell 1 flows through the image pickup area 10a, 10b. Hence, the operator can know accurately the volume of the sample liquid flowing through the image pickup area 10a, 10b. Also, the detection optical system is made simple as the width of the detection area 50a, 50b need not be changed. Consequently, the particle analyzing system can be made compact and the adjusting procedure can be simplified. The sample liquid 6 flows uniformly, with its width kept equal to the width of the image pickup area 10a, 10b in either mode. This means that the image pickup area 10a, 10b is used efficiently and increases the efficiency of analysis. Furthermore, whole particles are photographed since particles will never move near the ends of the image pickup area 10a, 10b. This makes image analysis accurate.

Figure 12:
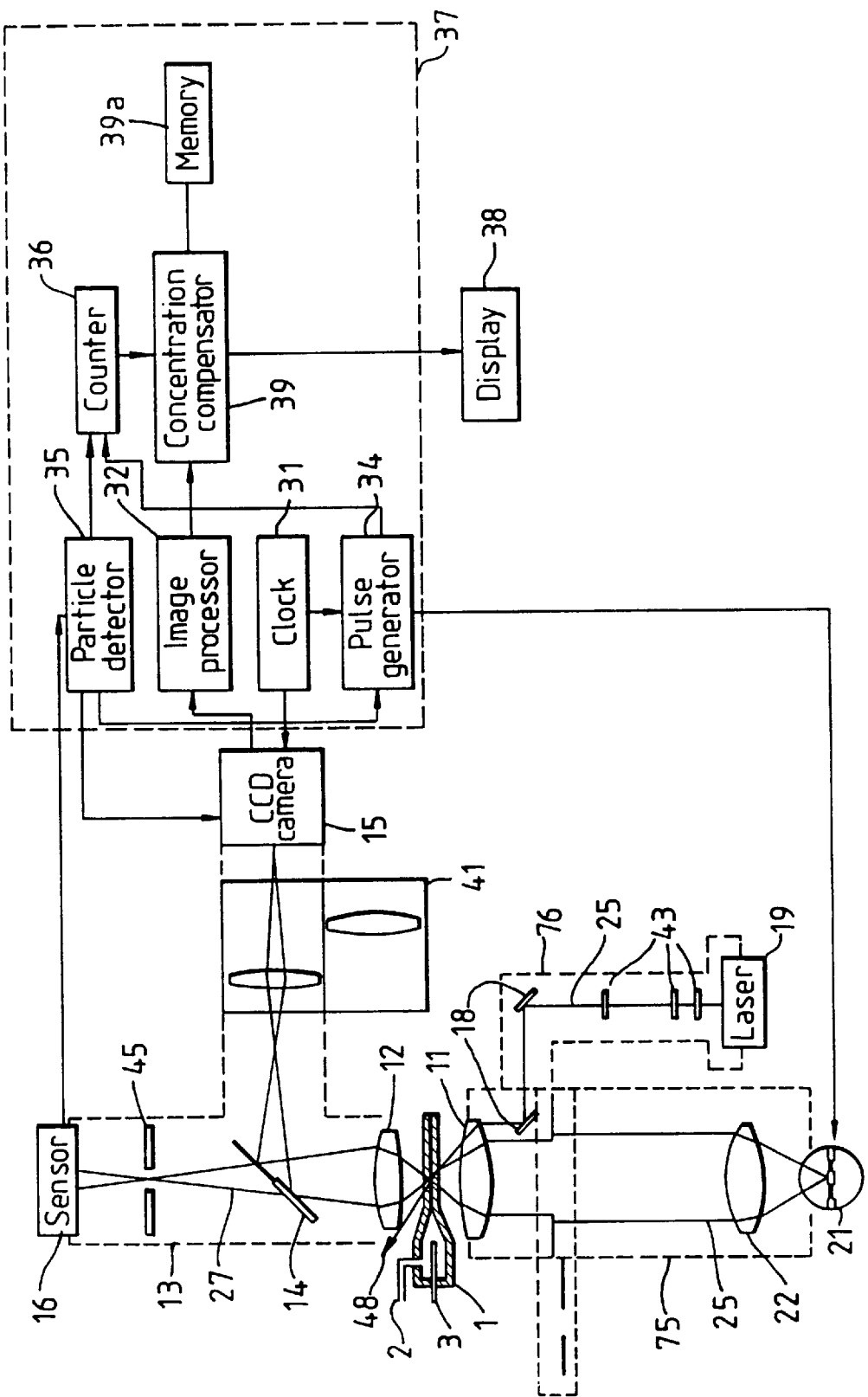
FIG. 12 illustrates the basic configuration of the detection system in a third embodiment of the present invention.

A third embodiment of the present invention will now be described with reference to FIG. 12 and FIG. 13. FIG. 12 illustrates the basic configuration of this embodiment and FIG. 13 shows an operational flow of analysis of particle concentrations. The configuration shown in FIG. 12 is generally similar to that of FIG. 4, and corresponding components are indicated by the same reference numerals. However, as can be seen in FIG. 12, a counter 36 is connected to the particle detector 35. The particle detector 35 detects a signal change of a preset level or higher and classifies it into a signal class by comparing its pattern to one or preset patterns. When the detected signal patterns belong to one of the preset signal classes, the particle detector 35 generates a timing signal. The signal classes which causes the particle detector 35 to generate a timing signal are specific to each magnification mode. After the particle detector 35 classifies the detected particle into a signal class, the counter 36 counts the number of timing signals for each signal class and sends the signal class of the particle detected by the particle detector 35 to the concentration compensator 39. If two or more particles are present in the image pickup area, all of the particles are image-analyzed and their shape classes are sent to the concentration compensator 39. The particle detector 35 also calculates the positions of particles in the view field and sends the result to the concentration compensator 39 together with the shape classes. (However, particles in a specific area in the view field are assumed to be in a range in which a target particle flows in a delay time starting from the continuous light emission area.) The concentration compensator 39 analyses particles in the specific area and stores their shapes and signal classes in the memory 39a.

After the above series of measurement, the concentration compensator 39 calculates the number of particles in a preset quantity of sample liquid from the number of particles photographed belonging to each shape class, the number of detected particles of each signal class, combinations of shape and signal classes, and the quantity of sample liquid fed to the flow cell 1 during measurement. The result is output to the display unit 38.

The count value of the counter 36 is used to obtain a particle concentration from the number of particles photographed. Although all particles passing through the flow cell 1 cannot be photographed, they can be all counted by the counter 36, from which the operator can obtain the number of particles in the sample liquid. By combining it with the ratio of particles obtained from image analysis of each type, the number of particles of each type can be estimated. Equation 7 (below) may thus be used to calculate the number of particles $C_j$ belonging to a shape class j.

$$C_j = \sum_{i=1}^{n_A} \frac{T_i P_{ij}}{\sum_{j=1}^{n_B} P_{ij}} \qquad \text{Equation 7}$$

$P_{ij}$ is the number of particles belonging to both shape class j and signal class i; and $T_i$ is the number of particles of signal class i which is counted by the counter 36;

$n_B$ is the number of shape classes; and $n_A$ is the number of signal classes.

As shown in FIG. 13, analysis of a specimen starts by resetting and initializing data stored in the image processor 32, the concentration compensator 39, and the counter 36. The operation starts in the Measurement mode, in which the particle detector 35, the image processor 32, and the counter 36 work in parallel while exchanging data. The particle detector 35 waits until a particle comes into the detection area, detects light scattered by a particle in the detection area, and classifies the pattern of the signal. The counter 36 increments the count $T_i$ of particles belonging to the detected signal class i.

If the detected particle triggers a photograph, the result of the classification of a signal class is set to the image processor 32. The image processor 32 checks whether photographing is performed in each field cycle. If photographing has not been performed, the image processor discards data of the field of the CCD camera 15 and enters the next field cycle. If photographing has been performed, data of two fields of the CCD camera 15 are sent to the image processor 32. The image processor synthesizes the data of two fields into a single static image, analyzes it to obtain the number of all particles in the image and classifies each particle into corresponding shape classes. The number of particles belonging to shape class j is added to $P_j$. Then, when a triggering particle is detected at a position in the view field, and it is added to $P_{ij}$ according to the shape class j of the particle and the signal class i determined by the particle detector 35. As the CCD camera performs photographing once for two fields, this process is performed within a 2-field cycle. The above operation is repeated until the end of measurement. At the end of measurement, the concentration compensator 39 calculates the number of particles of each shape class using Equation 7 and determines the concentration of particles of each type. This sequence of operations occurs in both Low and High Magnification modes under different conditions.

As this embodiment counts the number of particles flowing at high flow rate, the number of particles can be counted accurately and exact particle concentrations can be obtained even the sample liquid has a high particle concentration.

Furthermore, this embodiment counts the number of particles in all specimens supplied in the time of measurement, which enables calculation of a particle concentration from the number of particles in a sample volume greater than the view volume. This increases the accuracy of the determination of the concentration. Furthermore, this embodiment calculates the number of particles of shape class j corresponding to the type of the particle by using Equation 3. Hence, the concentration of particles of each type can be determined accurately.

Figure 14:
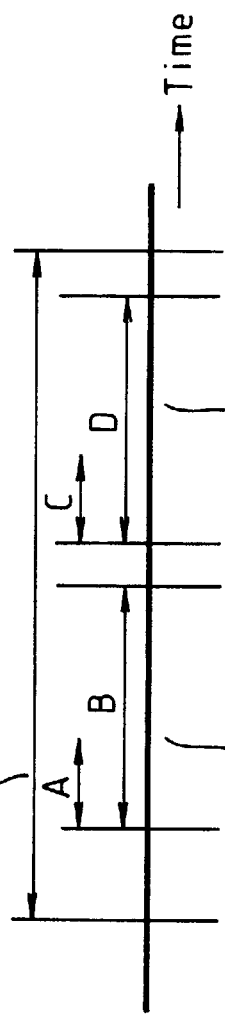
FIG. 14 is a timing chart showing the operation of a fourth embodiment of the present invention.

A fourth embodiment of the present invention will now be described with reference to FIG. 14. FIG. 14 shows the operation of the particle analyzing device during measurement of one specimen relative to the time base (the horizontal axis). The measurement of one specimen contains a period of measurement in the Low Magnification mode and a period of measurement in the High Magnification mode. Each period of measurement is further divided into two subperiods (A, B and C, D). The subperiods B and D are respectively as long as a period of measurement in the corresponding magnification mode. During subperiod B measurement of large particles of low concentration occurs and during subperiod D measurement of small particles of low concentration occurs. The subperiods A and C are respectively a part of period of measurement in the Low Magnification mode and a part of a time period of measurement in the High Magnification mode. During subperiod A measurement of large particles of high concentration occurs and during subperiod C measurement of small particles of high concentration occurs. Therefore, subperiods A, B, C, and D are respectively related to the signal classes of particles. A particle of a signal class is photographed only when it passes through the image pickup area in a corresponding period.

In a period corresponding to measurement in the Low Magnification mode, comparatively large particles are analyzed. Large particles that are frequently found in the sample liquid are photographed in subperiod A and large particles which are significant, although the quantity thereof is very small, are photographed in subperiod B. In the leading part of the period of measurement in the Low Magnification mode, all large particles are photographed. But in the trailing part of the period, particles of a type which are common in the sample are not photographed even when they are detected and only particles of a type which is not common are photographed.

During measurement in the High Magnification mode, comparatively small particles are photographed and analyzed. Small particles that are common in the sample liquid are photographed in subperiod C and small particles which are important, but are photographed in subperiod D. In the leading half of the period of measurement in the Low Magnification mode, all small particles are photographed. However, in the trailing half of the period, particles of a type which are common in the sample are not photographed even when they are detected and only particles of a type which is not common are photographed.

In the analysis of a liquid sample containing both high concentration particles and low concentration particles, this embodiment waits, without photographing until a low concentration particle is detected in the trailing half of the image pickup period. Accordingly, the chance of photographing low concentration particles increases and the number of images of such particles increases. Therefore, particles of low concentration can be shape-analyzed using a lot of images. This increases the accuracy of analysis. Furthermore, the concentration of even particles of low concentration can be analyzed with high precision since such particles have more likelihood of being photographed. For particles of high concentration, the large number of images required for accurate analysis can be obtained in part of the measurement period. Therefore, this embodiment can perform high precision analysis. The high concentration particles are counted throughout the whole measurement period, so the determination of the number of particles in the sample is very accurate. This enables high precision analysis.

In this embodiment, it is possible to vary the duration of the subperiod A or C (measurement in Low Magnification mode) instead of holding it constant. For example, it is possible to set an upper limit to the number of images photographed for each signal class and to stop photographing particles of the signal class if the number of images photographed exceeds the limit. In this way, a sample liquid having unknown particle concentrations can be analyzed efficiently by halting the photographing of particles of a signal class whose concentration is large and by photographing particles of low-concentration in the rest of the measurement period. Thus, even a sample liquid having various particle shapes and concentrations can be analyzed accurately for particles of any concentration.

Figure 15:
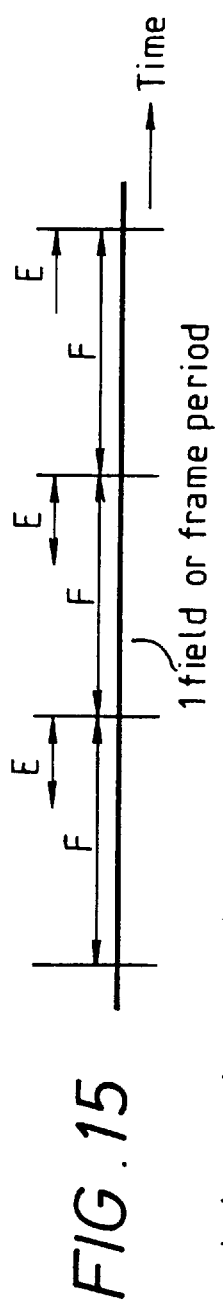
FIG. 15 is a timing chart showing the operation of a fifth embodiment of the present invention.

A fifth embodiment of the present invention will now be described with reference to FIG. 15. FIG. 15 shows field cycles or frame cycles of the CCD camera relative to the time base (the horizontal axis). Each frame cycle contains periods E and F. The period F is the same length as one frame cycle and the period E corresponding only to a trailing part of one frame cycle.

Periods E and F are related to signal classes of particles. In other words, period E is related to a signal class of high concentration particles and period F is related to a signal class of low concentration particles. In the leading half of the frame cycle, no high concentration particles are photographed even when they are detected but low concentration particles are photographed. When the period E, particles with a high concentration are photographed when they are detected. The period E is shortened when the particle concentration is high but lengthened when the particle concentration is low.

When a sample liquid having particles of both high- and low-concentration is analyzed by this embodiment, particles of low-concentration are preferentially photographed in the leading half of each frame cycle (when particles of high concentration are not photographed). Accordingly, particles of low concentration have more chance to be photographed and can be analyzed accurately. If no particles of low concentration pass in the frame cycle, particles of high concentration are photographed in the period E. Thus, particles of high concentration are photographed without reducing the chances of photographing particles of low concentration and particles of high concentration can also be analyzed with high precision.

If there is a frame cycle in which no image is photographed, an image processor which can only analyze one image in a frame cycle cannot analyze an image in that frame cycle and the number of particles to be analyzed reduces. However, in this embodiment, particles of high-concentration are photographed when no low concentration particles are detected in a frame cycle. Accordingly, the possibility that photographing does not occur in a frame cycle is very small. Thus, many particles can be image-analyzed efficiently.

Furthermore, this embodiment is not limited to arrangements in which the separate periods of the cycle are used to detect specific particles of a given size range, and all particles of the size range, respectively. The embodiment may also be used to investigate:
  a) particles which, in a first time period, have a predetermined property (e.g. shape or characteristic) and, in a second time period, particles having that predetermined property and being of a predetermined particle type; and/or
  b) particles which, in a first time period, have a particle size and being of one type and, in a second time period, particles of that size but being of another type.

A sixth embodiment of the present invention will now be described with reference to FIG. 16 to FIG. 18.

The general structure of this embodiment is similar to that of FIG. 4, and corresponding parts are indicated by the same reference numerals.

Figure 16:
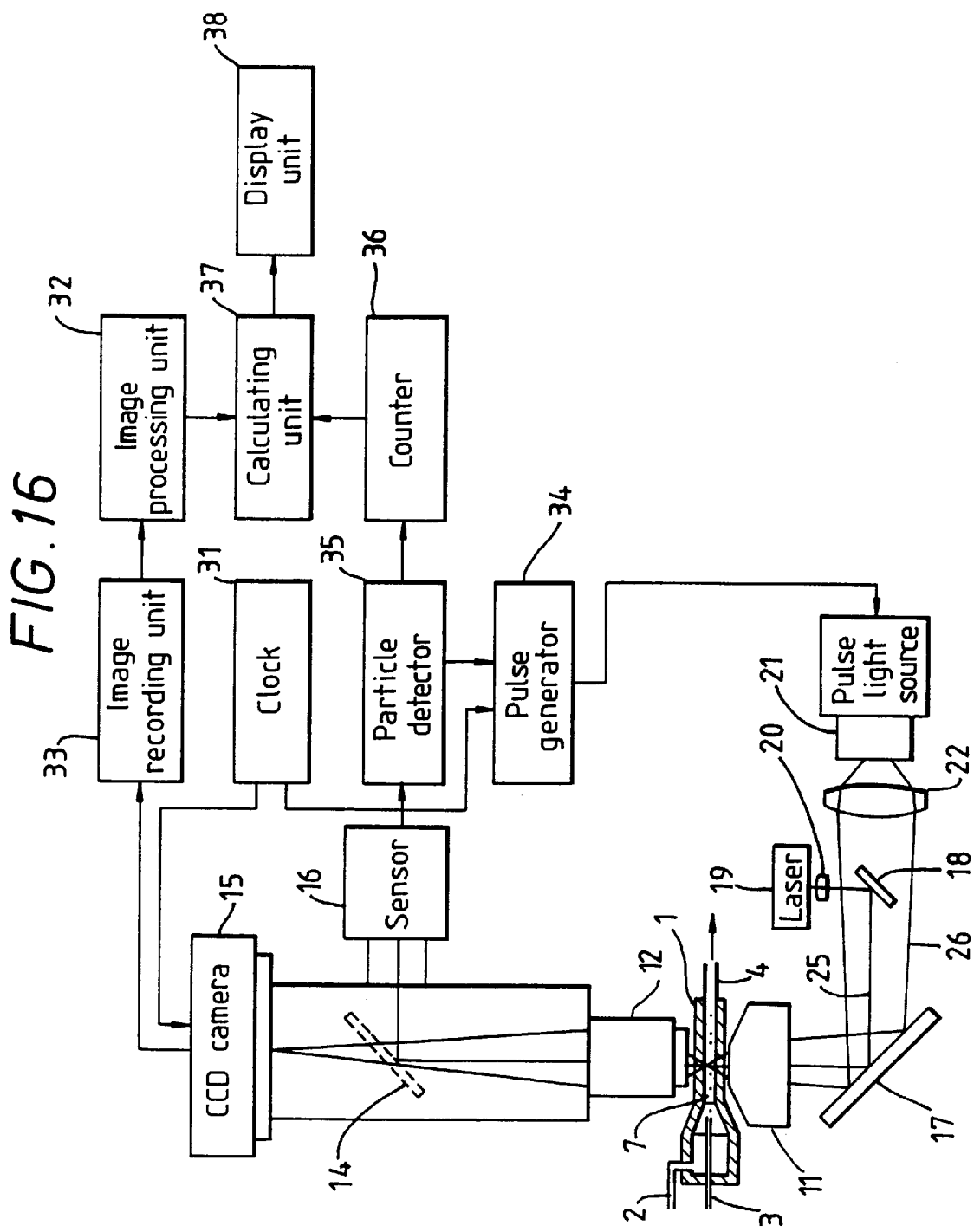
FIG. 16 illustrates the configuration of a sixth embodiment of the present invention.

As shown in FIG. 16, the upper and lower sides of the flow passage of a flow cell 1 of this embodiment are made of transparent glass and the flow cell is placed at the focus of a microscope 13. The flow cell 1 has a sample liquid inlet 3 and a sheath liquid inlet 2 which encloses the sample liquid inlet 3 at the center of the upstream end of the flow cell 1. Sample liquid having test particles suspended therein or dyed (when required) is fed into the flow cell at a constant rate through the sample liquid inlet 3 by a sample liquid supplying means (not shown). At the same time, clean liquid free from particles is fed at a constant rate through the sheath liquid inlet 2 by a clean liquid supplying means (not shown). A steady laminar flow (sheath flow) is formed inside the flow cell 1 in which the sheath liquid encloses the sample liquid. The particles 7 to be analyzed in the laminar flow are carried at a constant speed through the flow cell 1.

Two optical systems are placed on the side of the flow cell opposite to the microscope 13, one of those systems is a pulse light emission system comprising a pulse light source 21, a lens 22, a mirror 17. The other is a continuous light emission system comprising a laser 19, a lens 20, a mirror 18, and a mirror 17. A condenser lens 11 is common to the pulse light emission system and the continuous light. The pulse light emission system, including the condenser lens 11, forms a Koehler illumination system.

Continuous light 25 emitted from the continuous light emission system passes through the flow cell 1 and the objective lens 12, and is reflected by the semi-transparent mirror 14 into the sensor 16.

The microscope 13 has a semi-transparent mirror 14. The sensor 16 and the CCD camera 15 are mounted on the microscope 17 so that an image may be focused thereon, as shown in FIG. 16. An image recording unit 33 is connected to the CCD camera 15 and an image processor 32 is connected to the image recording unit 33. A particle detector 35 is connected to the sensor 16 so that a signal representing the intensity of light which hits the sensor 16 may be sent to the particle detector 35. The particle detector 35 is connected to a counter 36 and a pulse generator 34. The image processor 32 and the counter 36 are connected to a processing unit 37. The processing unit 37 is also connected to a display unit 38. A clock is connected to the CCD camera 15 and to the pulse generator 34. The pulse generator 34 is further connected to the pulse light source 21.

The pulse light emission system, including the condenser lens 11, also forms a Koehler illumination system. Continuous light 25 emitted from the continuous light emission system passes through the flow cell 1 and the objective lens 12, and is reflected by the semi-transparent mirror 14 into the sensor 16.

Figure 17:
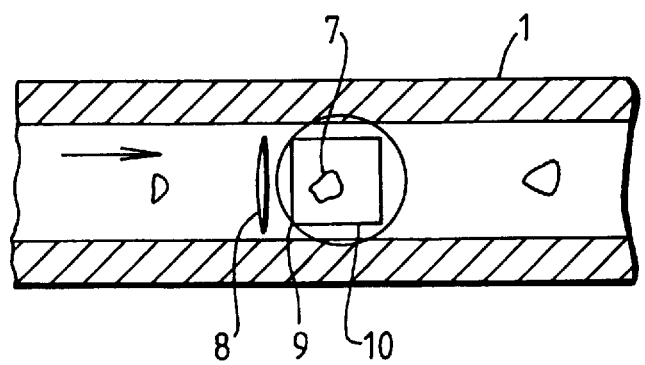
FIG. 17 is a sectional top view of the flow cell in the embodiment of FIG. 16.

FIG. 17 shows the top sectional view of the image pickup area. Light from this area focused into the CCD camera by the objective lens 12, via the semi-transparent mirror 14. The image pickup area 10 is contained with the pulse light emission area 9 onto which the pulse light is applied uniformly. The continuous light emission area 8 is always provided on the upstream side of the image pickup area 10.

When a particle 7 to be analyzed comes into the continuous light emission area 8 of the flow cell 1, the intensity of light incident upon the sensor 16 changes. The particle detector 35 details this change in light pattern, compares it with pre-stored light change patterns, and hence determines that a particle has passed through this area 8. When it is determined that the change of the light intensity matches one of the pre-stored patterns, the particle detector 35 recognizes that a particle 7 has passed through the area 8 and outputs a timing signal, together with a signal corresponding to the pattern which matches the light intensity change.

The counter 36 counts the number of timing signals generates for each pattern in dependence on the discriminating signal. At the end of the series of measurements, the counter outputs the result to the processing unit 37.

As shown in FIG. 18, the CCD camera 15 operates cyclically under the control of the clock 31. One cycle of the CCD camera 15 contains an image storage period in which the CCD camera stores the amounts of light incident upon its focal plane as an electric charge, and an image data transfer period in which the CCD camera transfers the electric charge to the image recording unit. After transferring the electric charge, the CCD has no electric charge and re-enters the image storage period.

Independently of the cyclic operation of the CCD camera 15, the particle detector 35 detects particles passing through the flow cell 1 and generates a timing signal. The pulse generator has a gate circuit. When a timing signal is received when the gate signal is "open", the pulse generator generates a Flash On pulse signal after a constant time delay equivalent to a time interval in which the particle moves from the continuous light emission area 8 to the center of the image pickup area 10 in the flow cell. This Flash On pulse signal causes the pulse light source 21 to emit light.

The gate signal is determined so as to be "open" when the CCD camera 15 enters an image storage period and to be "closed" when a timing signal is input. When the gate is "closed", it does not open until the CCD camera enters the next period. Furthermore, the gate circuit is designed so that it does not output a Flash On pulse signal when a timing signal is input while the gate is closed. Accordingly, the pulse light source 21 is designed so that only one flash occurs in one cycle of the CCD camera 15.

The CCD camera 15 stores an image of a particle 7 passing through the image pickup area 10 as an electric charge at the time when the pulse light source flashes and transfers them sample to the image recording unit 33. The image recording unit 33, which preferably is in the form of a semiconductor memory, stores data of one or more images and transfers the data to the image processor 32. The image processor 32 analyzes the image data and determines the type and properties (quality) of the particle 7 and outputs the result of analysis to the processing unit 37.

As described above, when the CCD camera 15 operates, the field cycle matches the frame cycle, but the photographing possibility $P_f$ of each field is expressed by Equation 8 below, rather than Equation 4.

$$P_f = 1 - e^{-m\lambda} \qquad \text{Equation 8}$$

Using Equation 8, the particle concentration is calculated from the number of particles photographed in the similar way to the first embodiment of the present invention.

The processing unit 37 calculates the ratios and numbers of particles of specific types and properties (qualities) from count values of each pattern sent from the counter 36 and the result of analysis sent from the image processor 32 and outputs the result to the display unit 38. The display unit can be either a CRT unit or a printer unit.

When this embodiment is applied to the analysis of particles in urine, images of almost still particles can be obtained by setting the size of the view field of the microscope 13 to be 1 mm×1 mm×0.02 mm, setting the moving speed of the particles to be 1 ms, the operating cycle of the CCD camera 15 to be 33 ms, and the flash-on time of the pulse light source 21 to be 1 µs (so that the particle moves 1 µm in the flash-on time).

A typical normal urine specimen contains one particle or less per 1 microliter. As the volume of sample liquid in one view field is 0.02 microliter, such a particle will rarely be found in the view field. On the other hand, if 0.66 microliter of sample liquid flows through the view field in one cycle of the CCD camera, there is a high possibility that the quantity of sample liquid contains such a particle. In this embodiment, the CCD camera is designed to wait for a particle during the image storage period and photograph a particle only at the time when the particle is at the center of the view field. With this arrangement, the operator can get images of particles efficiently even when the sample liquid has very low particle concentration.

For analysis of a diseased urine specimen, whose particle concentration is some hundred times that of a typical normal urine specimen, a lot of particles pass through the view field of the CCD camera in an image storage period. However, clear non-doubled images of particles can be obtained since the pulse light source 21 flashes once in the image storage period. These images can make the analysis of particle types easy. Also, all particles passing through the flow cell are counted by the counter 36. Hence, the operator can determines the total number of particles contained in the sample liquid, although all particles cannot be photographed. Hence, it is easy to estimate the number of particles of each type from the ratio obtained from the result of image analysis and this total number of particles.

Usually, urine specimens contain various kinds of particles and it is very important to analyze particles of different kinds. For example, if a column-like particle is found in 15 microliters of a urine specimen, this may suggest the existence of a fatal disease. In analysis of a hematuric specimen which contains lots of red blood cells, it is possible to configure this embodiment so that it does not photograph any red blood cell. This can be achieved if the particle detector 35, which detects particles by their light-intensity-change patterns, is set to ignore the small and short-lasting light intensity changes made by red blood cells but to photograph particles which have a large and long-lasting light intensity change, corresponding e.g. to column-like particle.

It is also possible to estimate the ratio of particles of every kind in a specimen by counting particles of each type, discriminating the particles by their intensity change patterns using the counter 36, and comparing them on the basis of the result of image analysis of each particle type.

As described above, this embodiment can perform satisfactory particle analysis on sample liquids having a wide range of particle concentrations. It is possible to estimate the concentrations of particles of every kind in the sample liquid. As this embodiment photographs the particles, and is not affected by intermittent or irregular flows of particles, the image recording unit can be an inexpensive general mass-storage medium such as a video tape recorder. This unit also enables later image analysis on screen.

As both the pulse light emission system and the continuous light emission system in this embodiment share a condenser lens and an objective lens, the device can be simple, compact, and low in production cost. Furthermore, the areas to be illuminated by the two emission systems can be placed very close to each other. This prevents the analysis from being influenced by uneven flow rate distribution and flow rate change in the flow cell 1.

In this embodiment, the operator can know the concentration of target particles in the sample liquid from the output of the particle detector before an image analysis is performed and change the flow rate of the sample liquid so as to get the optimum number of particles for analysis.

Figure 19:
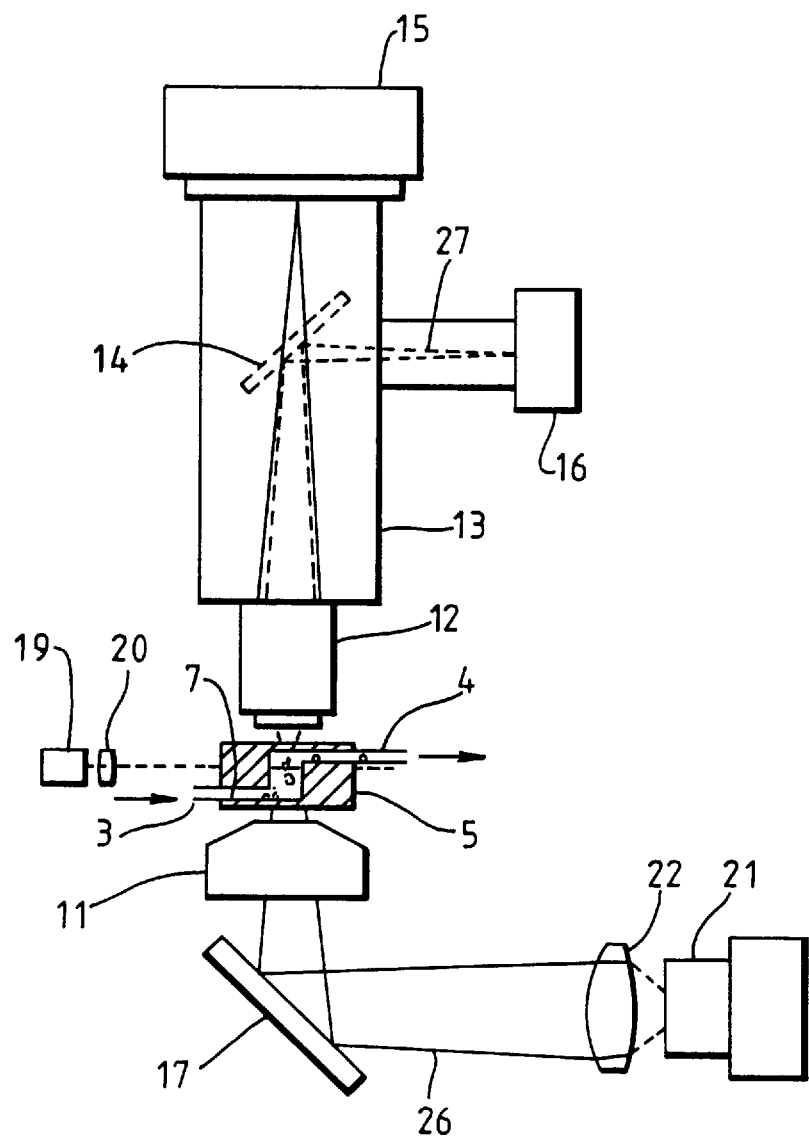
FIG. 19 illustrates the configuration of part of a seventh embodiment of the present invention.

A seventh embodiment of the present invention will now be described in detail with reference to FIG. 19. This embodiment is the same as the sixth embodiment except for the structure of the flow cell. In this embodiment, the transparent flow cell 5 is so structured so that the sample liquid may flow from the pulse light source 21 to the microscope 13 and that the laser light 19 may pass through the flow cell 5 laterally.

When a particle 7 to be analyzed comes into the continuous light emission area 8, light rays in the area 8 are scattered by the particle 7. The scattered light rays are focussed by the objective lens 12 to the sensor 16 and detected. The pulse light source 21 flashes at a constant delay time later, in dependence on the detected light pattern. The focal depth of the high resolution microscope is very small. Therefore, images of particles outside the thin image pickup area 10 are not clear. In this embodiment, however, sharp images can be obtained since particles 7 are photographed at the time when they are in the image pickup area 10.

Furthermore, in this embodiment, sample liquid flows vertically through the thin image pickup area 10. This can increase the cross section of the sample liquid flow. Consequently the number of particles passing through the image pickup area per unit time can be increased, which reduces the time of measurement. Furthermore, an increase in the cross section of the flow can reduce pressure loss in the flow cell 5.

Furthermore as continuous light 25 goes through the flow cell laterally, it never reaches the objective lens 12 directly. Only those light rays which have been scattered by a moving particle can reach the objective lens 12. In other words, no light signal reaches the sensor 16 unless a particle flows through the flow cell. Hence, even small particles can be detected with high sensitivity. Another advantage of this arrangement is that no unwanted light rays reach the CCD camera 15 and spoil the images.

Figure 20:
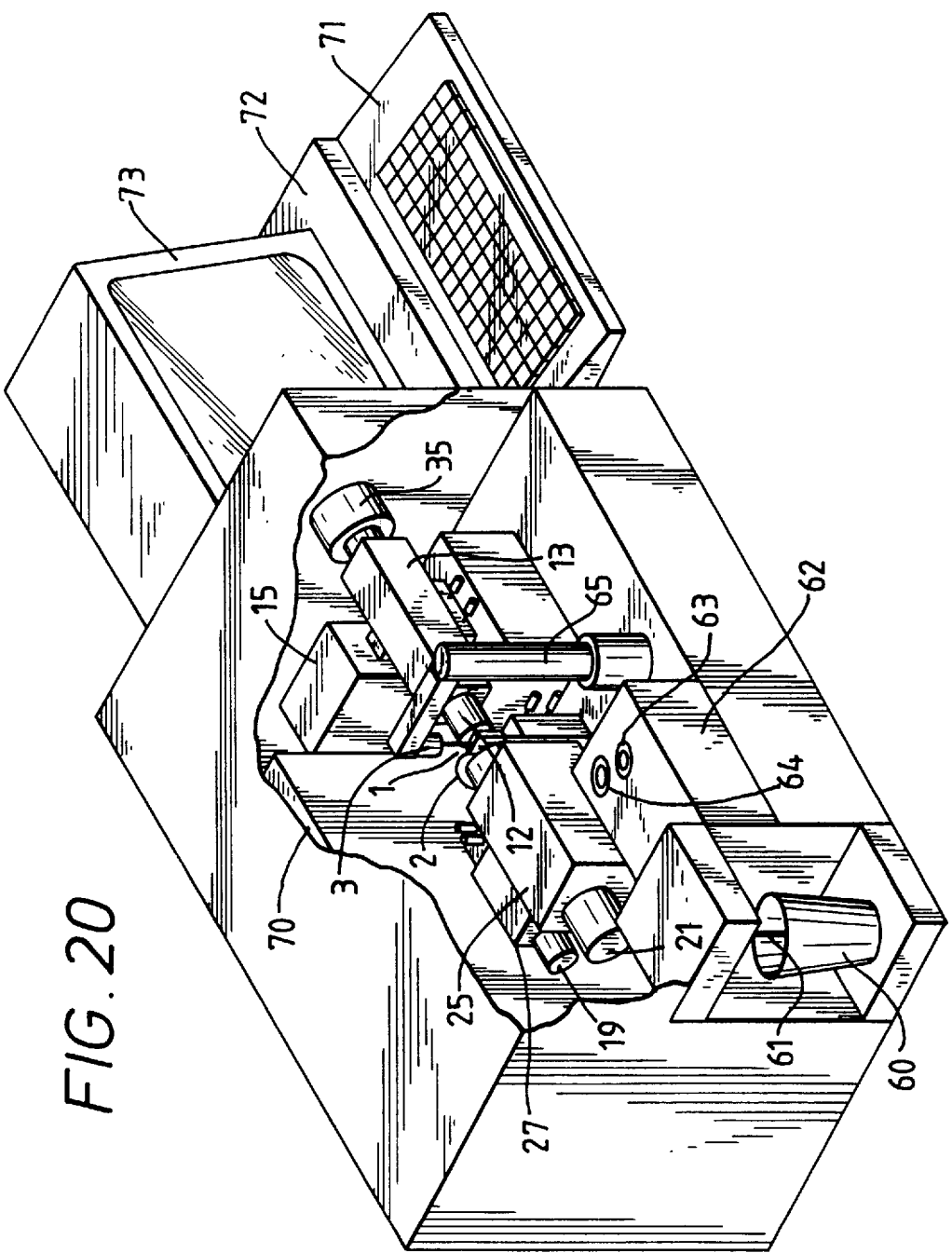
FIG. 20 is a perspective view of the structure of an eighth embodiment of the present invention.

A seventh embodiment of the present invention will now be described in detail with reference to FIG. 20. The embodiment shown in FIG. 20 uses a sample container 60 such as a cup instead of the sample disk 86 shown in FIG. 1 and such a sample container is placed directly in the preprocessor 87. This structure can operate without a sample disk 86 and its driving unit. Consequently the device can be more compact and lower in cost.

What is claimed is:

1. An apparatus for investigating particles mixed in a sample fluid, comprising:

a flow cell forming a flow path of said sample fluid therein;

a particle detector for detecting said particles flowing into an imaging domain of said flow path, so as to generate an output signal;

an image means for obtaining a particle number by scanning two-dimensionally said particles in said imaging domain in respective image storage periods of the image means on the basis of said output signal and for transferring said particle number in respective transfer periods after said respective image storage periods;

a storage means for storing compensation coefficients as a relationship of said particle number and a concentration of said particles; and an analysis means for modifying said particle number transferred from said image means, by using said compensation coefficients, so as to obtain a concentration of the particles in said sample fluid.

2. An apparatus for investigating particles as defined in claim 1, wherein said modifying said particle number is performed based on a total of said particle number transferred from said image means.

3. An apparatus for investigating particles as defined in claim 2, wherein said concentration is obtained from a total of said particles including particles which are not detected in said respective image storage periods.

4. An investigating method of particles mixed in a sample fluid, comprising the steps of:

forming a flow path of said sample fluid;

detecting said particles flowing into an imaging domain of said flow path, so as to generate an output signal;

obtaining a particle number by scanning two-dimensionally said particles in said imaging domain in respective image storage periods on the basis of said output signal, and transferring said particle number in respective transfer periods after said respective image storage periods;

storing compensation coefficients as a relationship of said particle number and a concentration of said particles; and modifying said particle number transferred in respective transfer periods, using said compensation coefficients, so as to obtain a concentration of the particles in said sample fluid.

5. An investigating method of particles mixed in a sample fluid as defined in claim 4, wherein the particles are detected by a particle detector that generates a continuous beam of light.

6. An investigating method of particles mixed in a sample fluid as defined in claim 5, wherein said obtaining a particle number includes generating an intermittent series of light pulses on the basis of said output signal and detecting interaction of said light pulses and said particles.

7. An investigating method of particles mixed in a sample fluid as defined in claim 4, wherein said obtaining a particle number includes forming an image of said particles, using an image device; and varying a magnification of the image device, and wherein at least one of a detection dimension of said detecting and a fluid flow rate at said forming an image is varied upon varying the magnification.

8. An investigating method of particles mixed in a sample fluid as defined in claim 7, wherein said detecting said particles is performed using a particle detecting device, and said varying the magnification is performed responsive to information from said particle detecting device.

9. An investigating method of particles mixed in a sample fluid as defined in claim 8, wherein two different types of particles are included in the sample fluid, and wherein said obtaining a particle number is performed for two different time periods.

10. An investigating method of particles mixed in a sample fluid as defined in claim 4, wherein two different types of particles are included in the sample fluid, and wherein said obtaining a particle number is performed for two different time periods.

* * * * *